(12) United States Patent
Clifton et al.

(10) Patent No.: US 9,615,749 B2
(45) Date of Patent: Apr. 11, 2017

(54) REMOTE MONITORING OF VITAL SIGNS

(75) Inventors: David Andrew Clifton, Oxford (GB); Mauricio Christian Villarroel Montoya, Oxford (GB); Lionel Tarassenko, Oxford (GB)

(73) Assignee: ISIS INNOVATION LIMITED, Oxford, Oxfordshire (GB)

( * ) Notice: Subject to any disclaimer, the term of this patent is extended or adjusted under 35 U.S.C. 154(b) by 494 days.

(21) Appl. No.: 14/240,291

(22) PCT Filed: Aug. 16, 2012

(86) PCT No.: PCT/GB2012/052004
§ 371 (c)(1),
(2), (4) Date: May 7, 2014

(87) PCT Pub. No.: WO2013/027027
PCT Pub. Date: Feb. 28, 2013

(65) Prior Publication Data
US 2014/0303454 A1    Oct. 9, 2014

(30) Foreign Application Priority Data

Aug. 22, 2011 (GB) .................................. 1114406.0

(51) Int. Cl.
*A61B 5/1455* (2006.01)
*A61B 5/02* (2006.01)
(Continued)

(52) U.S. Cl.
CPC .......... *A61B 5/0077* (2013.01); *A61B 5/0022* (2013.01); *A61B 5/0205* (2013.01);
(Continued)

(58) Field of Classification Search
CPC ... A61B 5/7203; A61B 5/0077; A61B 5/0205; A61B 5/1176; A61B 5/14551; A61B 5/0022
See application file for complete search history.

(56) References Cited

U.S. PATENT DOCUMENTS 5,107,845 A    4/1992   Guern et al.
5,954,644 A    9/1999   Dettling et al.
(Continued)

FOREIGN PATENT DOCUMENTS

EP    2346387 A1    7/2011
EP    2 438 849 A1  4/2012
(Continued)

OTHER PUBLICATIONS

International Preliminary Report on Patentability regading Application No. PCT/GB2012/052004 dated Mar. 6, 2014.
(Continued)

*Primary Examiner* — Eric Winakur
(74) *Attorney, Agent, or Firm* — Harness, Dickey & Pierce, P.L.C.

(57) ABSTRACT

A method of remote monitoring of vital signs by detecting the PPG signal in an image of a subject taken by a video camera such as a webcam. The PPG signal is identified by auto-regressive analysis of ambient light reflected from a region of interest on the subject's skin. Frequency components of the ambient light and aliasing artefacts resulting from the frame rate of the video camera are cancelled by auto-regressive analysis of ambient light reflected from a region of interest not on the subject's skin, e.g. in the background. This reveals the spectral content of the ambient light allowing identification of the subject's PPG signal. Heart rate, oxygen saturation and breathing rate are obtained (Continued)

from the PPG signal. The values can be combined into a wellness index based on a statistical analysis of the values.

16 Claims, 23 Drawing Sheets

(51) Int. Cl.
| | |
|---|---|
| A61B 5/00 | (2006.01) |
| A61B 5/0205 | (2006.01) |
| A61B 5/024 | (2006.01) |
| A61B 5/08 | (2006.01) |
| A61B 5/1171 | (2016.01) |
| G06T 5/00 | (2006.01) |
| G06T 5/10 | (2006.01) |
| G06K 9/00 | (2006.01) |

(52) U.S. Cl.
CPC ........ *A61B 5/02416* (2013.01); *A61B 5/0816* (2013.01); *A61B 5/1176* (2013.01); *A61B 5/14551* (2013.01); *A61B 5/7203* (2013.01); *A61B 5/725* (2013.01); *G06K 9/00563* (2013.01); *G06T 5/008* (2013.01); *G06T 5/10* (2013.01); *G06T 2207/10016* (2013.01); *G06T 2207/10024* (2013.01); *G06T 2207/30076* (2013.01); *G06T 2207/30088* (2013.01); *G06T 2207/30104* (2013.01); *G06T 2207/30201* (2013.01)

(56) References Cited

U.S. PATENT DOCUMENTS

| | | | |
|---|---|---|---|
| 8,503,712 | B2 | 8/2013 | Ahmed et al. |
| 2002/0030154 | A1 | 3/2002 | Marchitto et al. |
| 2002/0120207 | A1 | 8/2002 | Hoffman |
| 2007/0156060 | A1 | 7/2007 | Cervantes |
| 2008/0045818 | A1 | 2/2008 | Wood et al. |
| 2008/0077020 | A1 | 3/2008 | Young et al. |
| 2009/0203998 | A1 | 8/2009 | Klinghult et al. |
| 2010/0268056 | A1 | 10/2010 | Picard et al. |
| 2010/0268094 | A1 | 10/2010 | Hasling et al. |
| 2010/0298730 | A1 | 11/2010 | Tarassenko et al. |
| 2011/0077482 | A1 | 3/2011 | Hsieh et al. |
| 2011/0098933 | A1 | 4/2011 | Ochs |
| 2012/0029322 | A1 | 2/2012 | Wartena et al. |
| 2012/0155716 | A1 | 6/2012 | Kim |
| 2012/0190944 | A1 | 7/2012 | Thaveeprungsriporn et al. |
| 2012/0190947 | A1 | 7/2012 | Chon et al. |
| 2013/0018240 | A1 | 1/2013 | McCoy |
| 2013/0215244 | A1* | 8/2013 | Mestha .................. H04N 7/18 348/77 |

FOREIGN PATENT DOCUMENTS

| | | |
|---|---|---|
| EP | 2617354 A1 | 7/2013 |
| FR | 2974289 A1 | 10/2012 |
| KR | 20060111159 A | 10/2006 |
| KR | 100880392 B1 | 1/2009 |
| TW | 201114238 A | 4/2011 |
| WO | WO-2009/016334 A1 | 2/2009 |
| WO | WO-2009/109185 A1 | 9/2009 |
| WO | WO-2010100593 A1 | 9/2010 |
| WO | WO-2010100594 A2 | 9/2010 |
| WO | WO-2011021128 A2 | 2/2011 |
| WO | WO-2011026986 A1 | 3/2011 |
| WO | WO-2011/042839 A1 | 4/2011 |
| WO | WO-2011042844 A1 | 4/2011 |
| WO | WO-2011042851 A1 | 4/2011 |
| WO | WO-2011042858 A1 | 4/2011 |
| WO | WO-2012093304 A1 | 7/2012 |
| WO | WO-2012093358 A1 | 7/2012 |
| WO | WO-2013027027 A2 | 2/2013 |
| WO | WO-2013093686 A1 | 6/2013 |
| WO | WO-2013128345 A1 | 9/2013 |
| WO | WO-2013136231 A1 | 9/2013 |
| WO | WO-2013156908 A1 | 10/2013 |

OTHER PUBLICATIONS

Tarassenko L, Clifton DA, Pinsky MR, Hravnak MT, Woods JR, Watkinson P. Centile-based early warning scores derived from statistical distributions of vital signs, Resuscitation, 2011, 82(8), 1013-1018.
Ibridge Network "Ambient Light/Non Contact Remote Pulse Oximeter".
Affective Computing, MIT Media Lab, pp. 1-4.
Your Vital Signs, on Camera, MIT News Office, pp. 1-3, David L. Chandler, MIT News Office, Oct. 4, 2010.
Smarter Than You Think—When Computers Keep Watch—NYTimes.com, pp. 1-7, Steve Lohr, Jan. 1, 2011.
Poh, Ming-Zher, et al: "Non-contact, automated cardiac pulse measurements using video imaging and blind source separation," Optics Express, OSA (Optical Society of America), Washington DC, (US), vol. 18. No. 10. May 10, 2010 (May 10, 2010), pp. 10762-10774, XP002686060, ISSN: 1094-4087, DOI: 10.1364/OE.18.010762.
Schmitz, G.L.L.H., "Video Camera based Photoplethysmography using Ambient Light," published 2011, Eindhoven University of Technology. Available from http://alexandria.tue.nl/repository/books/710886.pdf [Accessed Dec. 14, 2011].
Fleming, S.G., et al, "30th Annual International IEEE EMBS Conferences," Vancouver, British Columbia, Canada, Aug. 20-24, 2008. pp. 1886-1889 "Non-invasive measurement of respiratory rate in children using the photoplethysmogram". See whole document, particularly section III on p. 1888.
Fleming, S.G. and Tarassenko, L., "A comparison of signal processing techniques for the extraction of breathing rate from the photoplethysmogram," International Journal of Biological and Medical Science, vol. 2, No. 4, 2007, pp. 276 to 280. See whole document, particularly section C "Novel AR method" from p. 277, col. 2 to p. 279, col. 1.
Verkruysse, W., Svaasand, L.O., and Nelson, J.S., "Remote plethysmographic imaging using ambient light," *Optics Express*, 2008, 16(26), 21434-45.
Wieringa, F.P., Mastik, F., and Van Der Steen, A.F.W., Contactless Multiple Wavelength Photoplethysmographic Imaging: A First Step Toward "SpO$_2$ Camera" Technology, *Annals of Biomedical Engineering*, 2005, 33(8), 1034-1041.
Humphreys, K., Ward, T., Markham, C., Noncontact simultaneous dual wavelength photoplethysmography: A further step toward noncontact pulse oximetry, *Rev. Sci. Instrum.*, 2007, 78, 044304.
Poh, M.Z., McDuff, D.J., Picard, R.W., Advancements in noncontact, multi-parameter physiological measurements using a webcam, *IEEE Trans Biomed Eng.*, 2011, 58, 7-11.
Pardey, J., Roberts, S., Tarassenko, L, A review of parametric modelling techniques for EEG analysis, *Medical Engineering & Physics*, 1996, 18(1), 2-11.
International Search Report and Written Opinion for PCT/GB2012/052004, mailed Feb. 15, 2013; ISA/EP.
Search Report of the British Intellectual Property Office for priority application GB 1114406.0 dated Dec. 16, 2011.
Search Report of the British Intellectual Property Office for priority application GB 1114406.0 dated Aug. 1, 2012.
Search Report of the British Intellectual Property Office for priority application GB 1114406.0 dated Aug. 2, 2012.

\* cited by examiner

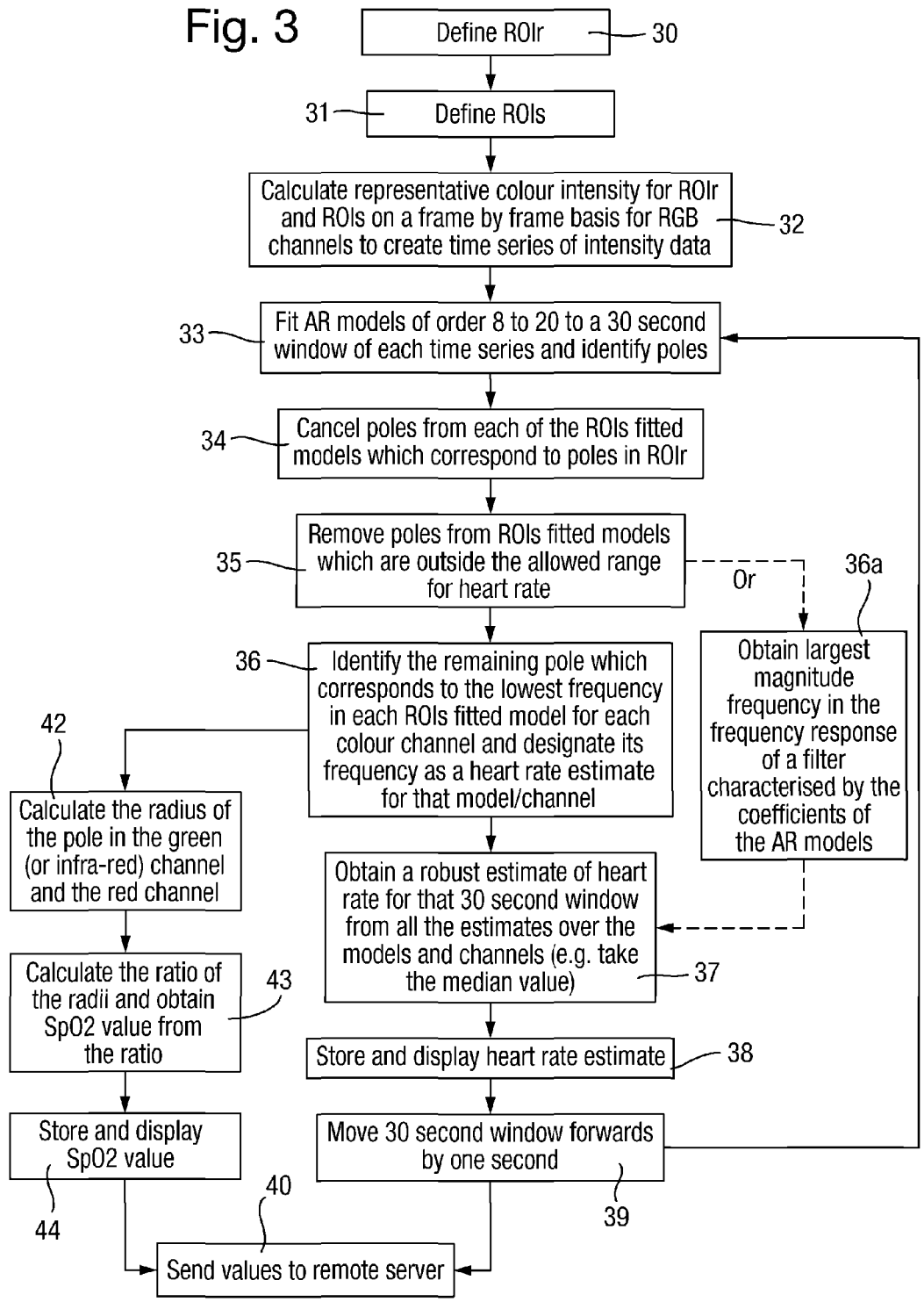

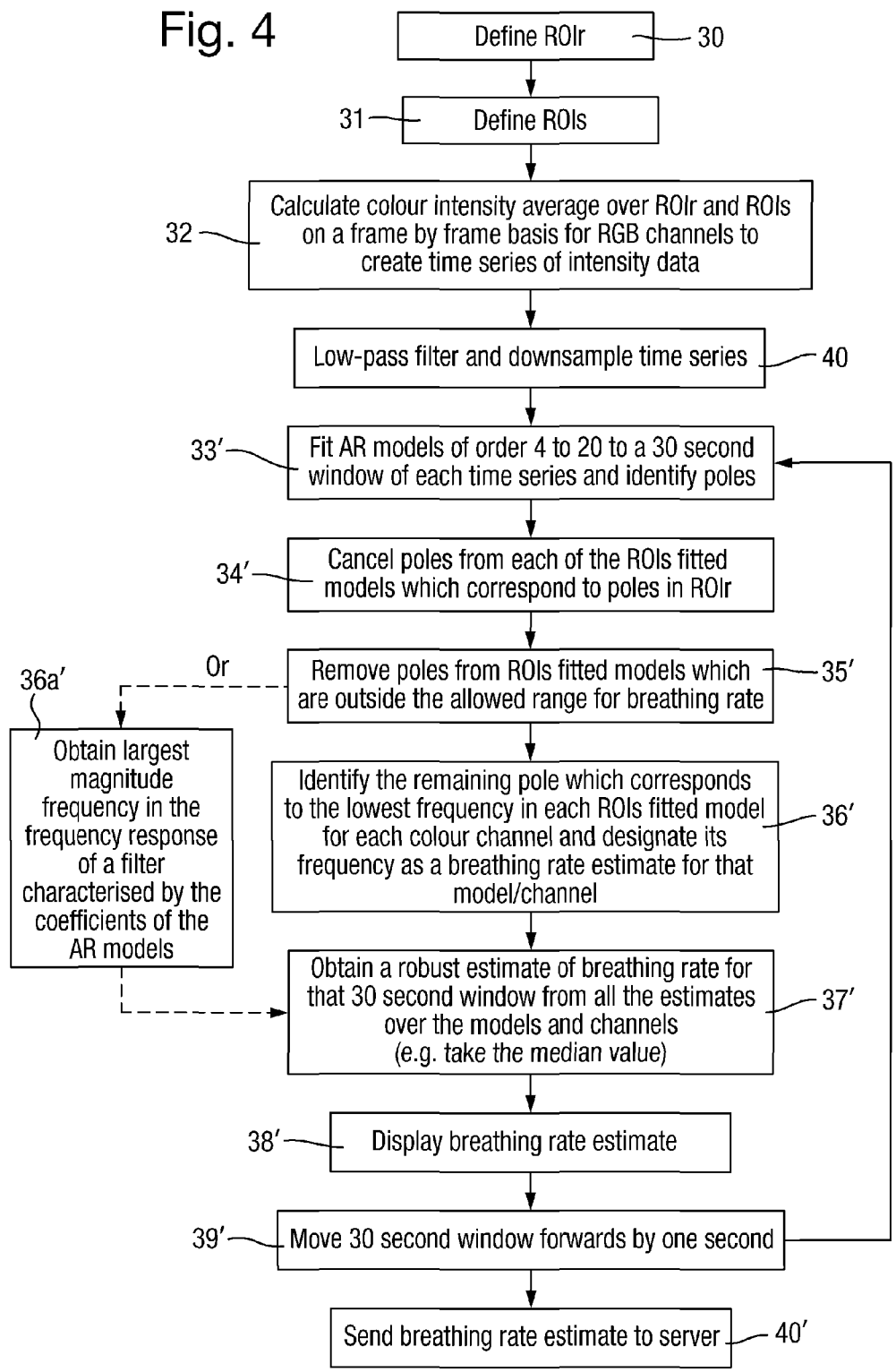

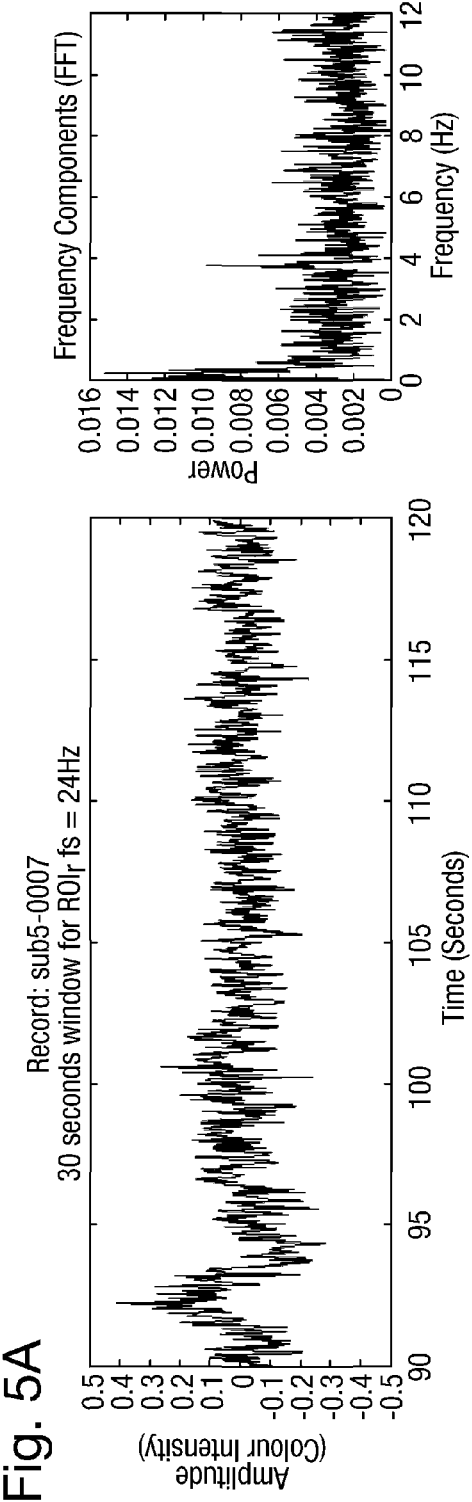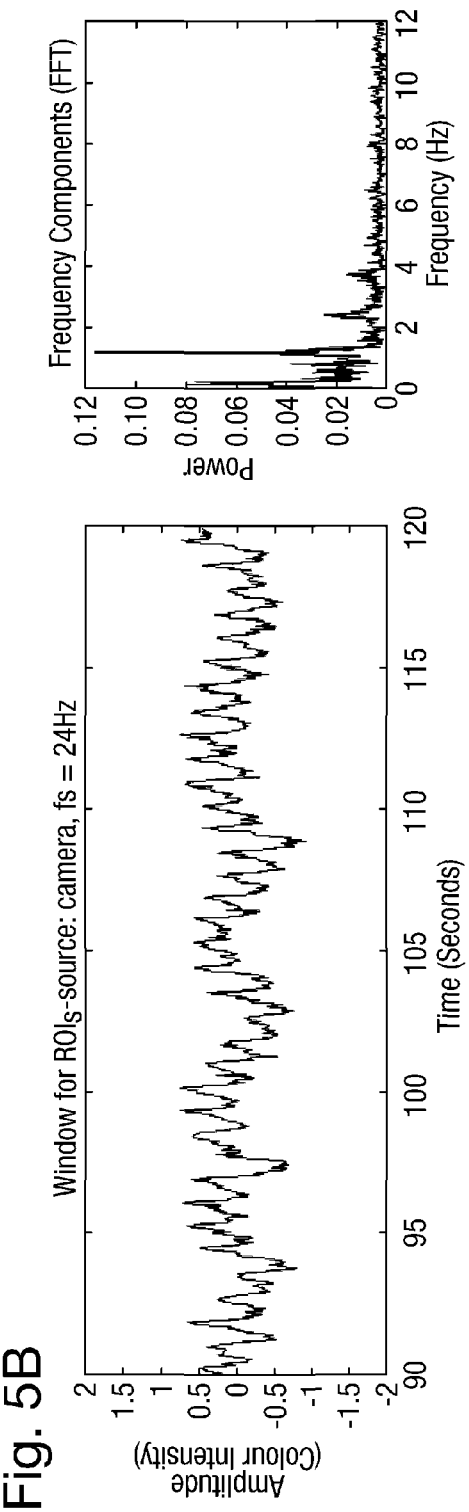
Fig. 5A
Fig. 5B

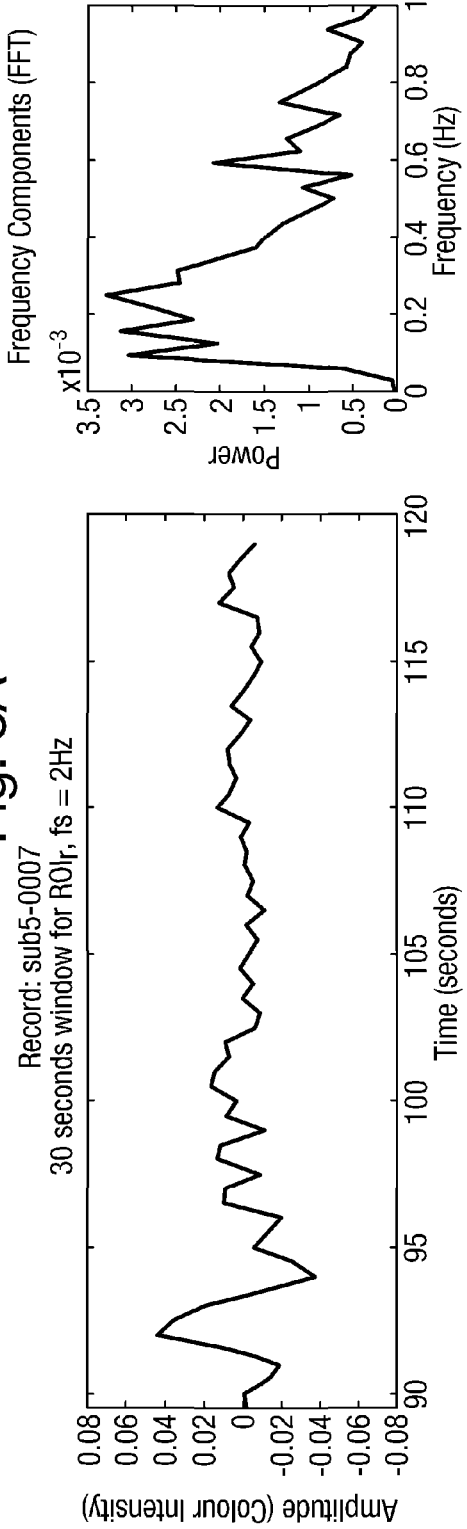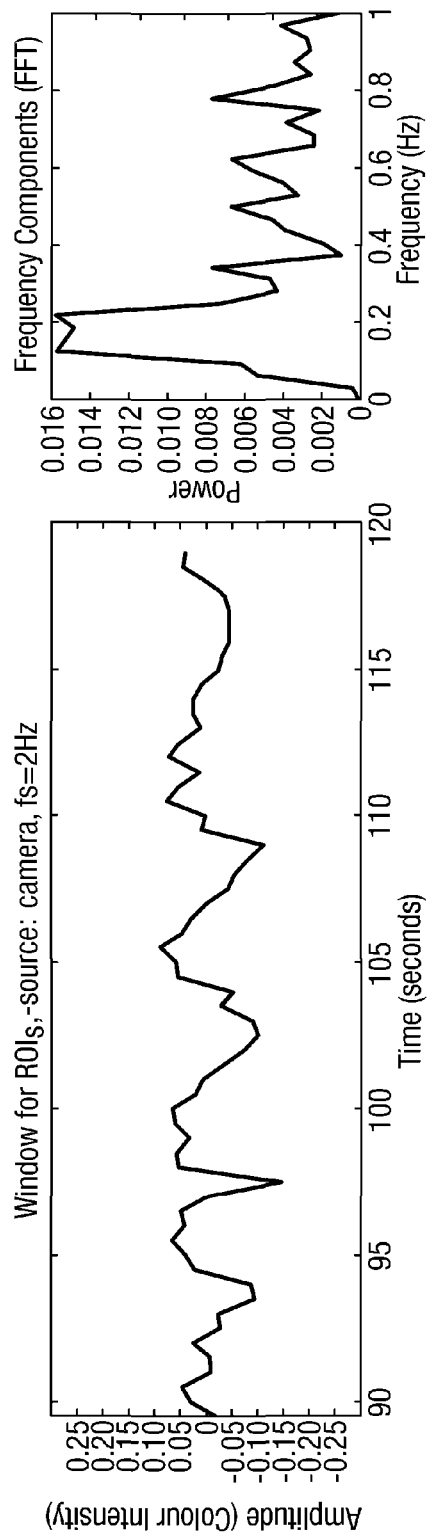
Fig. 8A
Fig. 8B

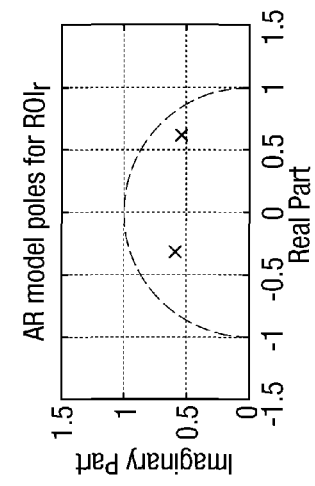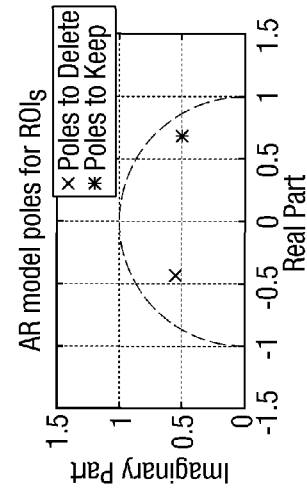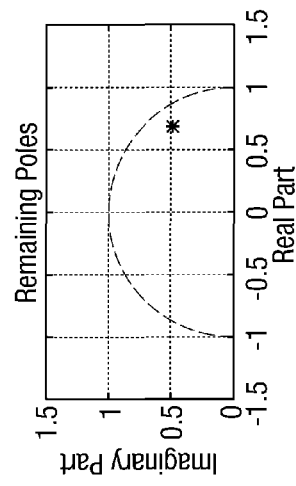
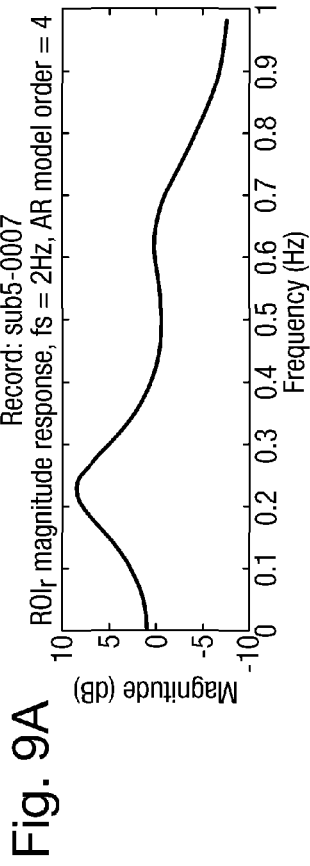
Fig. 9A
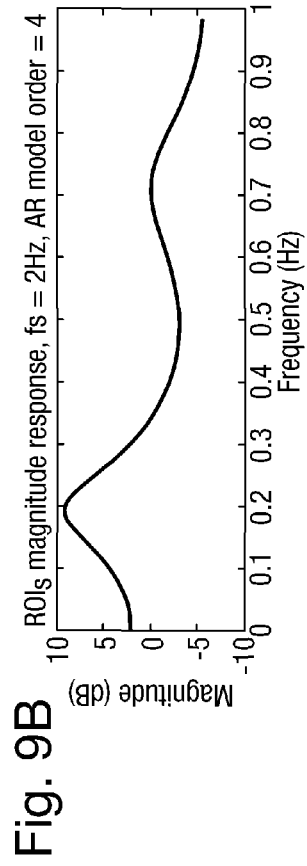
Fig. 9B
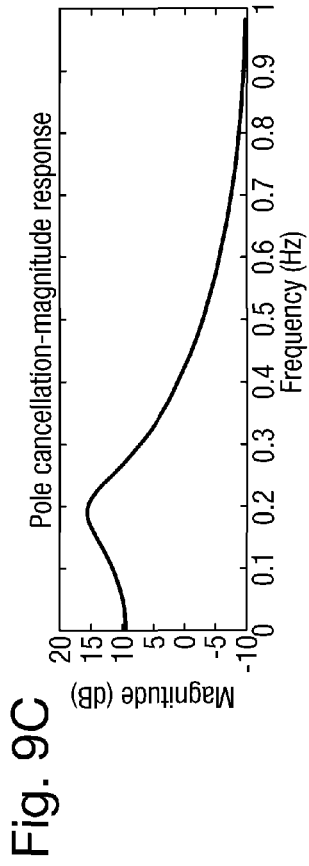
Fig. 9C

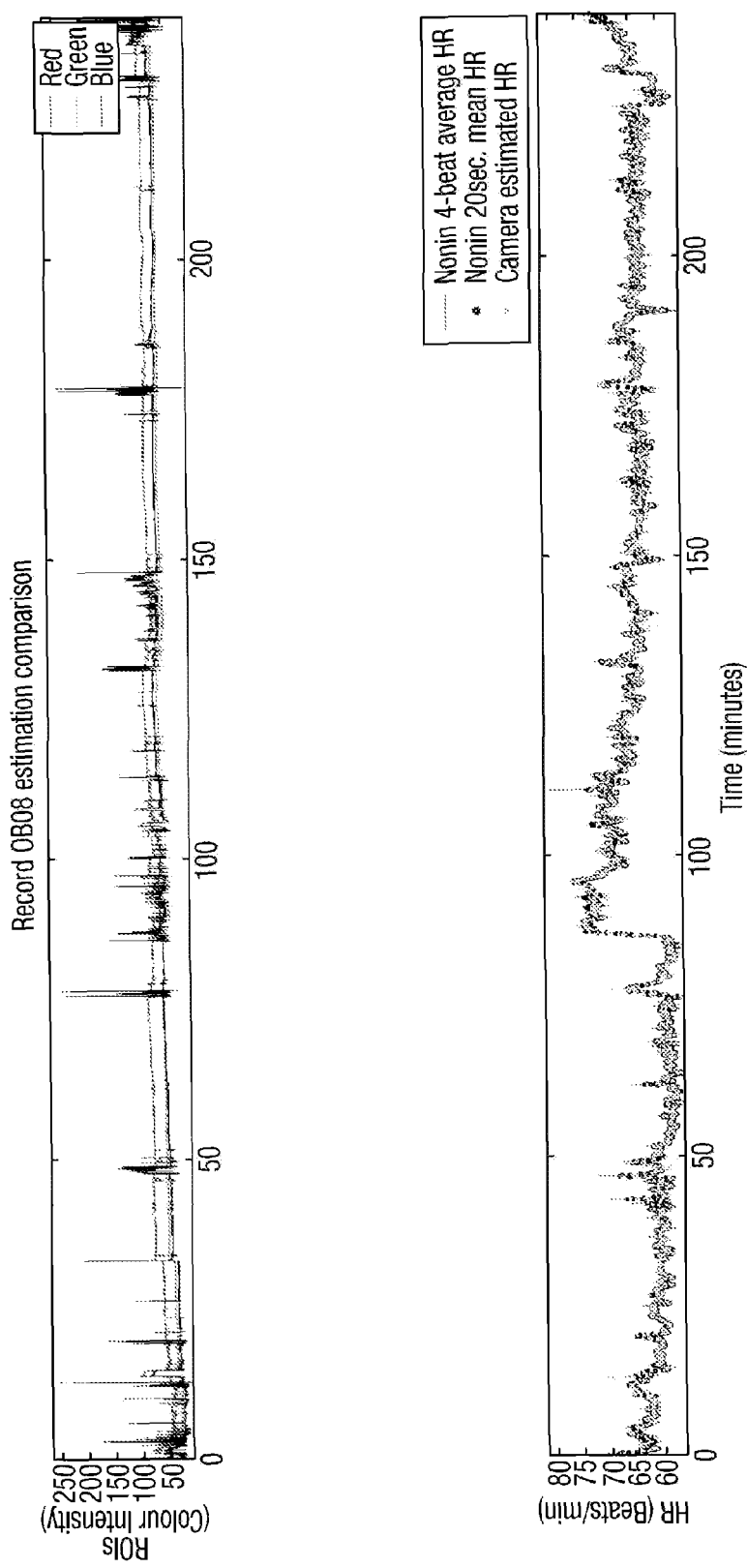

REMOTE MONITORING OF VITAL SIGNS

CROSS-REFERENCE TO RELATED APPLICATIONS

This application is a 371 U.S. National Stage of International Application No. PCT/GB2012/052004 filed on Aug. 16, 2012, which claims priority to British Patent Application No. 1114406.0, filed on Aug. 22, 2011. The contents of the above applications are incorporated herein by reference in their entirety.

The present invention relates to the remote monitoring of human (or animal) vital signs such as heart rate, breathing rate and arterial oxygen saturation, and in particular to obtaining improved measurements from a photoplethysmogram image signal by removing the effects of ambient light interference.

It is clear from working with patients with moderate-to-severe long-term conditions (such as Chronic Obstructive Pulmonary Disease or Congestive Heart Failure) that they find it difficult to self-monitor on a regular basis. Probes are often difficult to attach and the process of recording the vital signs (one or more of heart rate, breathing rate, oxygen saturation or blood pressure), even if it only takes a few minutes, becomes burdensome as it usually has to be performed on a daily basis. The ideal technology would involve no direct contact with the patient ("non-contact sensing") and would be seamlessly integrated into the patient's lifestyle.

It has been well known since the 1930s—see the introduction in the paper by Verkruysse W, Svaasand L O and Nelson J S entitled "Remote plethysmographic imaging using ambient light", *Optics Express*, 2008, 16(26), 21434-45—that the variations in blood volume in a body segment with each heart beat modulate the reflection or transmission of visible (or infra-red) light through that body segment. Blood absorbs visible and infra-red light more than the surrounding tissue in the body segment, hence the variations in blood volume during the cardiac cycle affect the transmission or reflectance of light in time with the heart beat. The cardiac-synchronous variations in light transmission or reflectance are known as the photoplethysmographic (hereafter PPG) signal. The heart rate (or pulse rate—the two are equivalent) can easily be extracted from the PPG signal by measuring the time interval between two consecutive peaks (or troughs) of the PPG waveform. The respiratory (or breathing) rate can also be estimated indirectly from relatively complex analysis of the PPG waveform, (for example, by measuring the changes in inter-beat interval which occur over the respiratory cycle) or by measuring the breathing-rate-synchronous amplitude modulation of the PPG signal.

In the 1970s, the technique of pulse oximetry was developed to obtain a non-invasive estimate of peripheral arterial oxygen saturation ($SpO_2$) by measuring the PPG signal at two wavelengths. The two common forms of the haemoglobin molecule (the oxygen carrier in the blood), oxidised haemoglobin ($HbO_2$) and reduced haemoglobin (Hb), have significantly different optical spectra in the wavelength range from 500 nm to 1000 nm. Hence, by measuring the light transmitted through the fingertip (or the earlobe) at two different wavelengths using a simple probe with two light-emitting diodes, one in the red and the other in the near infra-red, pulse oximeters determine the oxygen saturation of the arterial blood in the finger (or ear) non-invasively.

The possibility of measuring PPG signals remotely using a camera (rather than a probe attached to the finger, ear or toe) is first discussed in the scientific literature around 2005 (see Wiering a FP, Mastik F and Van Der Steen AFW, Contactless Multiple Wavelength Photoplethysmographic Imaging: A First Step Toward "$SpO_2$ Camera" Technology, *Annals of Biomedical Engineering*, 2005, 33(8), 1034-1041 and Humphreys K, Ward T, Markham C, Noncontact simultaneous dual wavelength photoplethysmography: A further step toward noncontact pulse oximetry, *Rev. Sci. Instrum.*, 2007, 78, 044304). In the 2008 paper from Verkruysse, Svaasand and Nelson mentioned above, the authors show that PPG signals can be remotely acquired from the human face with normal ambient light as the source and a simple, digital, consumer-level camera as the detector more than 11 m away. Regions of interest (usually the forehead) were selected in images of the faces of human volunteers. The paper shows how heart rate can be extracted from the frequency content of these images (using the Fast Fourier Transform for 10-sec windows), and hints at how breathing rate may be computed. They suggest that the main application of this remote sensing technology might be in triage and sports.

In the last year, there have been two papers published by a team from the Affective Computing group (http://www-.media.mit.edu/research/groups/affective-computing) in the MIT Media Lab. (see Poh M Z, McDuff D J, Picard R W, Non-contact, automated cardiac pulse measurements using video imaging and blind source separation, *Optics Express*, 2010, 18, 10762-10744 and Poh M Z, McDuff D J, Picard R W, Advancements in noncontact, multi-parameter physiological measurements using a webcam, *IEEE Trans Biomed Eng.*, 2011, 58, 7-11). The team have recorded videos of facial regions with a webcam. They focus on sources of fluctuations in light due to artefacts caused by motion and changes in ambient light conditions. Although their experiments were carried out indoors, the only source of illumination was a varying amount of ambient sunlight entering through windows.

A serious problem with making PPG imaging work in real-world settings is the ambient light interference from artificial light, e.g. fluorescent light, found in most indoor environments outside daylight hours and often within daylight hours as well. Although the 50 Hz frequency of intensity variation is much higher than the heart rate or breathing rate vital signs being measured (even the fastest heart rate is unlikely to be faster than 4 Hz=240 beats per minute (bpm)), in practice the intensity variations are aliased down to much lower frequencies because of the sampling process. The image is sampled at the video camera's frame rate, typically approximately 24 Hz, which is much lower than the sampling frequency which would be required (100 Hz) to avoid aliasing of the 50 Hz light and aliasing components (artefacts) are often found at frequencies such as 4 Hz and 2 Hz. However it is not possible to predict exactly what frequencies will result from this aliasing process so it is not effective simply to filter at specific frequencies, as the filters would need to be re-tuned in each setting to track the aliasing artifacts.

The present invention therefore provides a way of identifying and removing spectral components in the PPG image signal which result from artificial (ambient) light interference. It also provides an elegant and simple way of obtaining the actual PPG signal frequency which corresponds to the heart rate. Another aspect uses a similar method to obtain a breathing rate measurement from the PPG image signal. It is also possible with the invention to obtain a measurement of the peripheral arterial blood oxygen saturation $SpO_2$.

The invention also allows these measurements to be combined into a single, easily-understandable wellness index.

Thus in more detail a first aspect of the present invention provides a method of suppressing ambient light interference in a PPG image signal comprising the steps of: imaging a region of interest on a subject's body using a video camera to obtain a PPG image signal comprising periodic intensity variations in ambient light reflected from the region of interest; imaging a reference region of interest not on the subject's body using the same video camera to obtain a reference signal; spectrally analysing the reference signal using an auto-regressive (AR) all pole model and identifying poles corresponding to spectral components; spectrally analysing the PPG image signal using an auto-regressive (AR) all-pole model to identify poles corresponding to spectral components therein and cancelling poles corresponding to those identified as spectral components of the reference signal.

The region of interest on the subject corresponds to an area of exposed skin, e.g. the face, and the reference region of interest is not on the skin. The reference region of interest can be in the image background, or on the subject's clothing. The invention can use an algorithm for automatically identifying areas of human skin in the image, such algorithms being widely commercially available.

Preferably the reference signal and PPG signal are the output signals from at least one of the red, green and blue channels of the video camera.

It is possible to have a plurality of regions of interest on the subject body, and optionally also a plurality of reference regions of interest. Again the results from the plurality of regions of interest, obtained by using respective sets of AR models for each region of interest on the subject's body to produce heart rate, breathing rate and oxygen saturation estimates, can be averaged. Each region of interest can be sized as desired, from one pixel to many, and the shape is not restricted. In one example of the invention the regions are each 100 by 100 pixels (i.e. 10,000 pixels total).

Preferably the method includes the step of obtaining vital-sign data, such as heart rate, breathing rate or oxygen saturation from the components of the PPG signal which remain after pole cancellation. The correct pole can be identified by looking for poles in the expected frequency range, for example for heart rate 40 to 240 bpm (0.67 to 4 Hz) or for breathing rate 3.6 to 42 breaths per minute (0.06 Hz to 0.7 Hz), though the specific limits can be varied.

In the step of spectrally analysing the reference signal and PPG image signal, preferably several AR models of different order are fitted to the signal and the results averaged. For example, thirteen models of order 8 to 20 are used in one example, or seven models of order 5 to 11 in another, though again different numbers and orders can be used in order to achieve the best fit to the data.

To obtain an accurate measurement of breathing rate it is preferable to low-pass filter and downsample the PPG signal before spectrally analysing it using the AR model or models. This effectively reduces the sampling frequency and so increases the angular separation between the pole corresponding to the breathing rate signal and DC (0 Hz)—represented in a pole plot by the positive half of the horizontal axis.

The oxygen saturation $SpO_2$ measurement can be obtained by calculating the ratio of the intensity of the reflected light at two different wavelengths. The intensity is found from the radius of the pole corresponding to the heart rate (i.e. its distance from the origin). The two different wavelengths can be the red and green channels from the video camera, or alternatively the red video camera channel can be used together with an infrared measurement from a second video camera.

The invention is preferably incorporated into a vital-sign monitor, which may be embodied as a computer program for running on a personal computer, tablet or laptop computer, or mobile telephone, and utilises a webcam incorporated into such a device.

The invention will be further described by way of example with reference to the accompanying drawings in which:—

FIG. 1A schematically illustrates a vital-sign monitoring system according to an embodiment of the invention;

FIG. 1B schematically illustrates the image obtained by the patient's device and the defined regions of interest;

FIG. 1C schematically illustrates a vital-sign monitoring system according to another embodiment of the invention;

FIG. 3 is a flow diagram explaining heart rate and oxygen saturation measurement according to one embodiment of the invention;

FIG. 4 is a flow diagram explaining breathing rate measurement according to one embodiment of the invention;

Figure 6A:
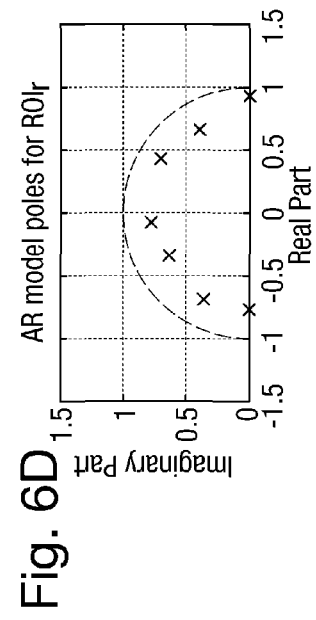
Figure 6B:
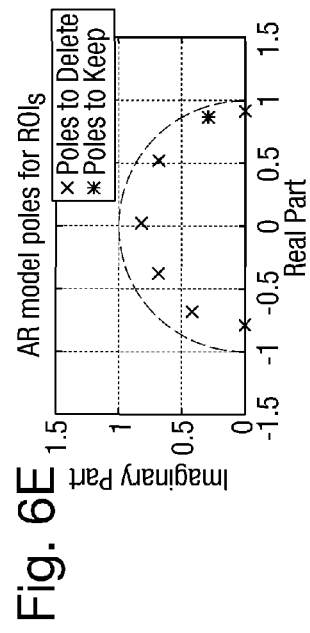
Figure 6C:
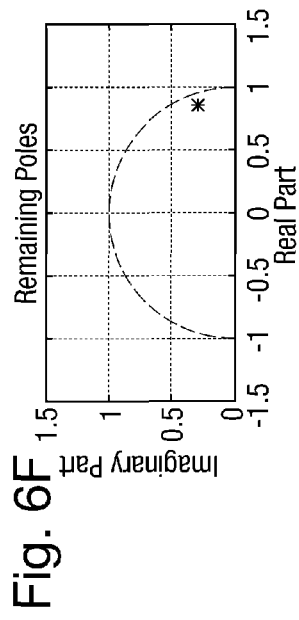
Figure 6D:
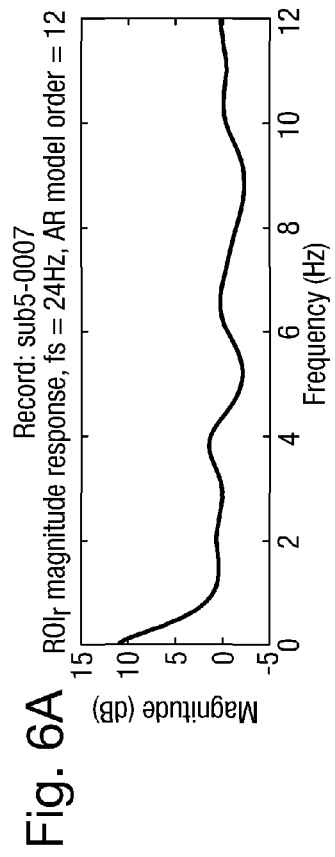
Figure 6E:
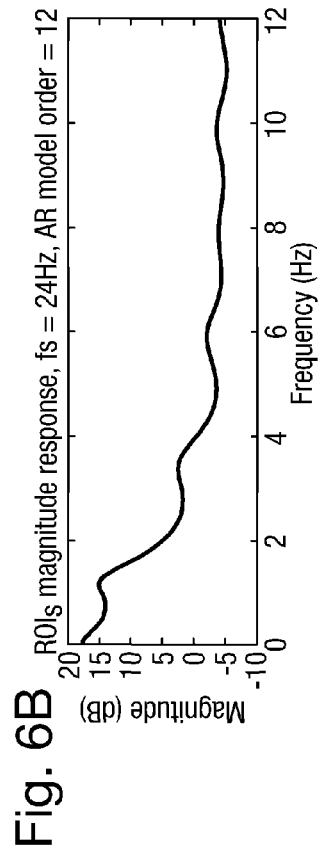
Figure 6F:
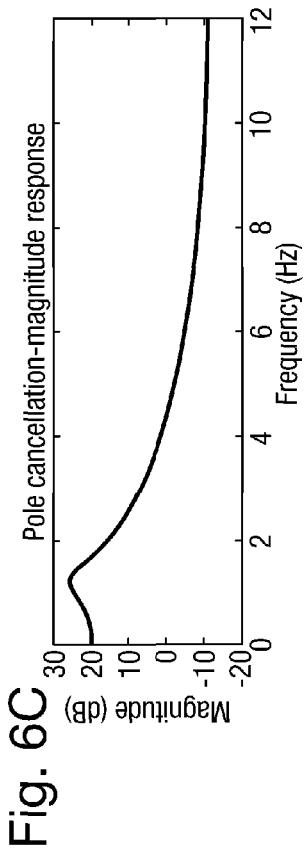
Figure 7:
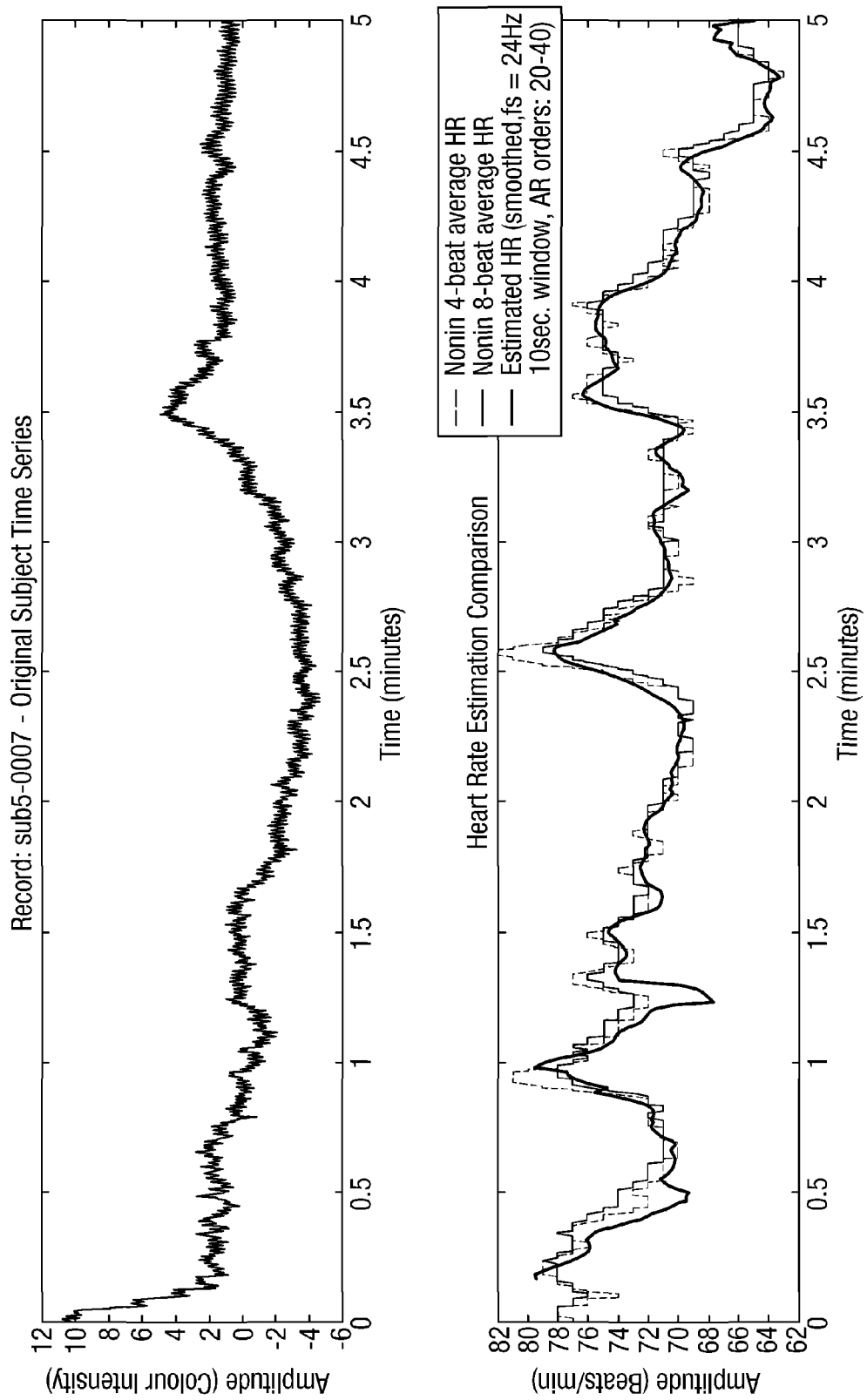
Figure 10:
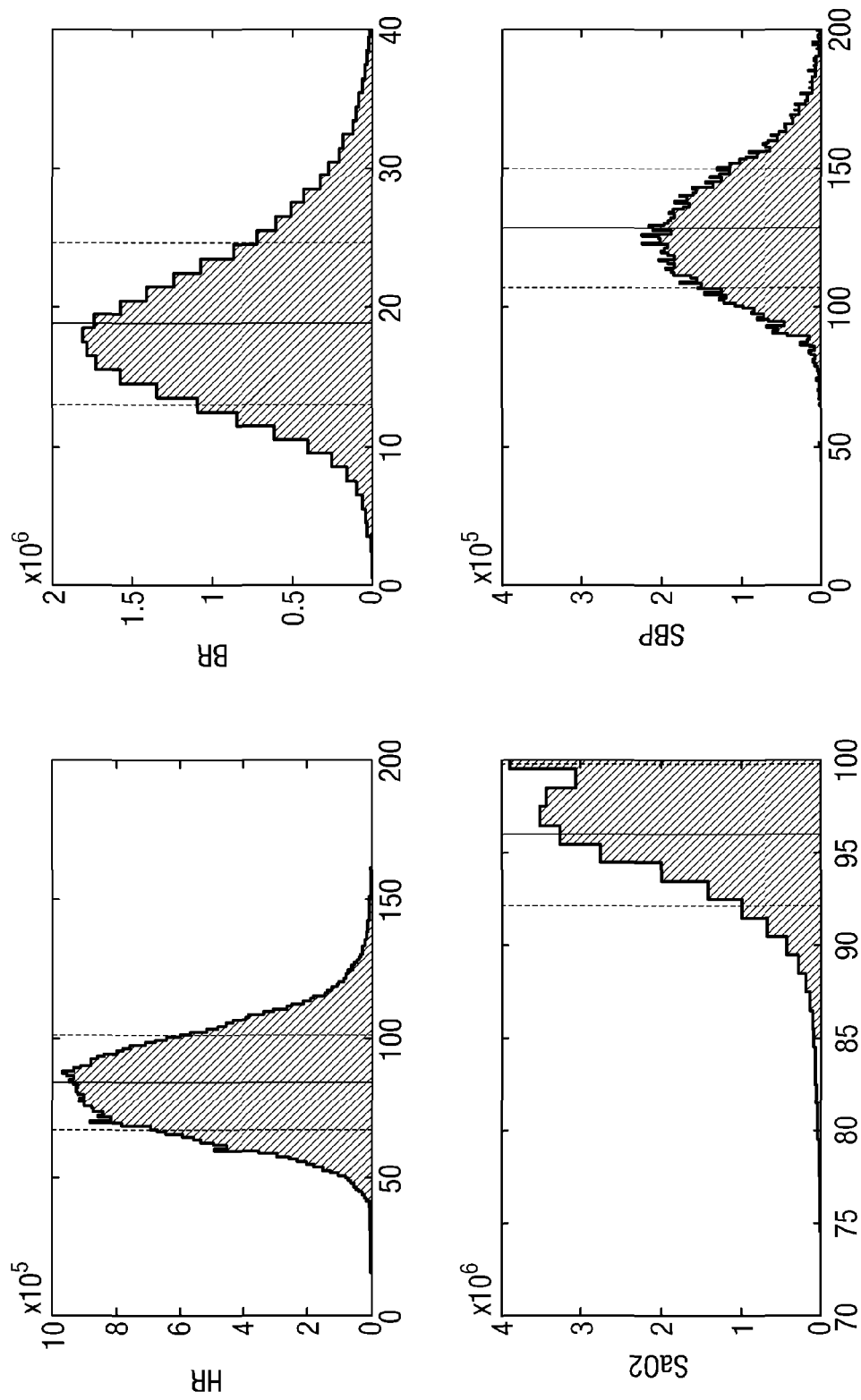
Figure 11:
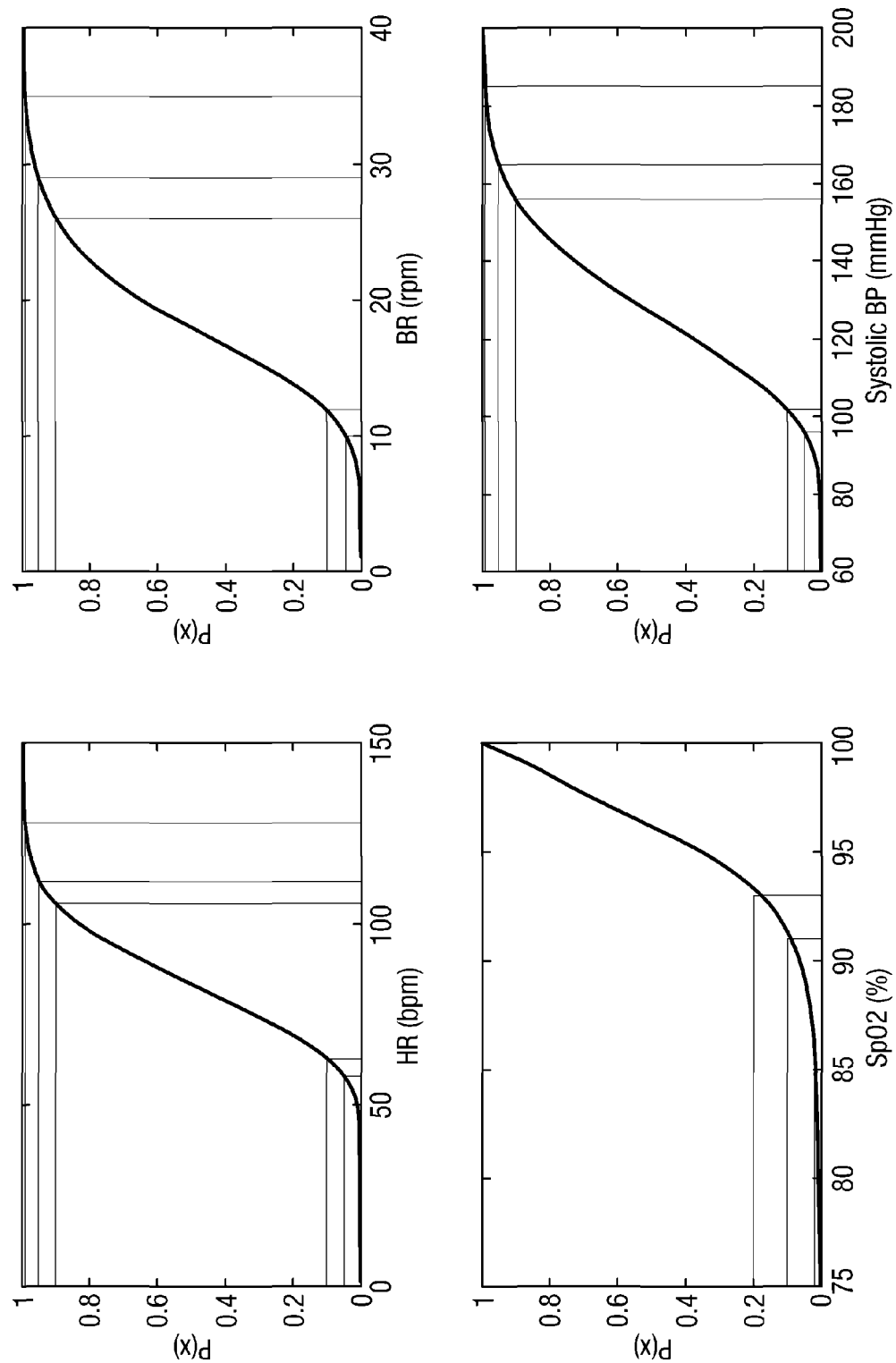
Figure 12:
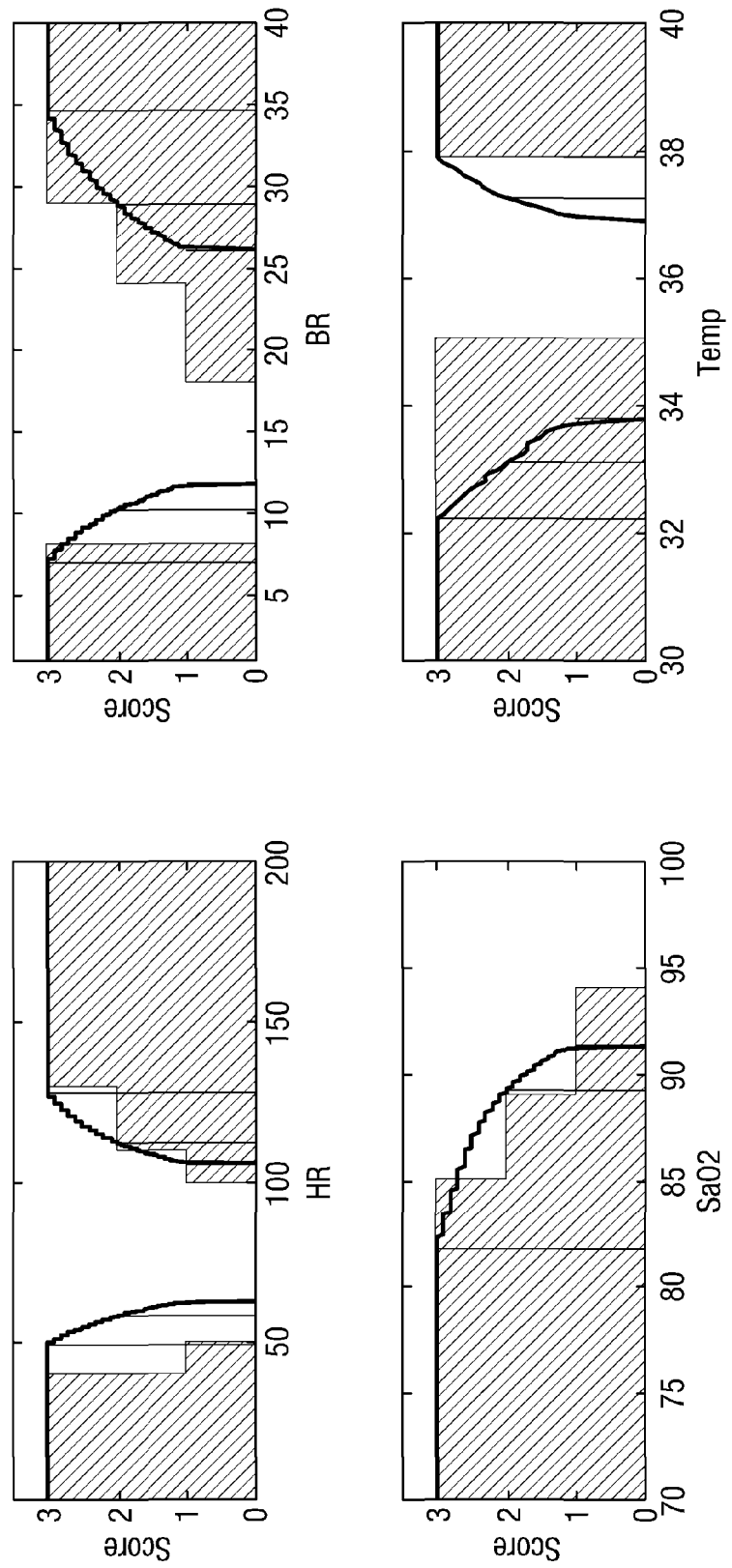

FIGS. 5A and 5B respectively show 30-second time series of data for the reference region of interest and for the subject region of interest;

FIGS. 6A and 6B illustrate respectively the spectral content of the reference and subject regions of interest obtained by fitting the twelfth-order AR model to the 30-second window of data of FIGS. 5A and 5B;

FIGS. 6D and 6E show the position of the poles derived from this twelfth-order model;

FIGS. 6C and 6F show the spectral content and poles remaining after cancellation of poles found in the reference signal;

FIG. 7A illustrates five minutes of colour intensity measurements and FIG. 7B illustrates a comparison of the 30-second mean heart rate estimates obtained by the embodiment of the invention above from that data with average heart rate measurements from a standard pulse oximeter;

FIGS. 8A and 8B illustrate downsampled time series of the FIG. 5 data;

FIGS. 9A, 9B and 9C illustrate the pole plots for respectively the reference region of interest, the subject region of interest, and for the subject region of interest after cancellation of the poles corresponding to those found in the reference region of interest;

FIG. 10 shows histograms for the four main vital signs: heart rate, breathing rate, arterial oxygen saturation and systolic blood pressure, obtained from patients in acute care in three hospitals in the UK and the US;

FIG. 11 illustrates cumulative density functions for each vital sign of FIG. 10; and FIG. 12 illustrates a set of curves for an Early Warning Score.

Figure 13A:
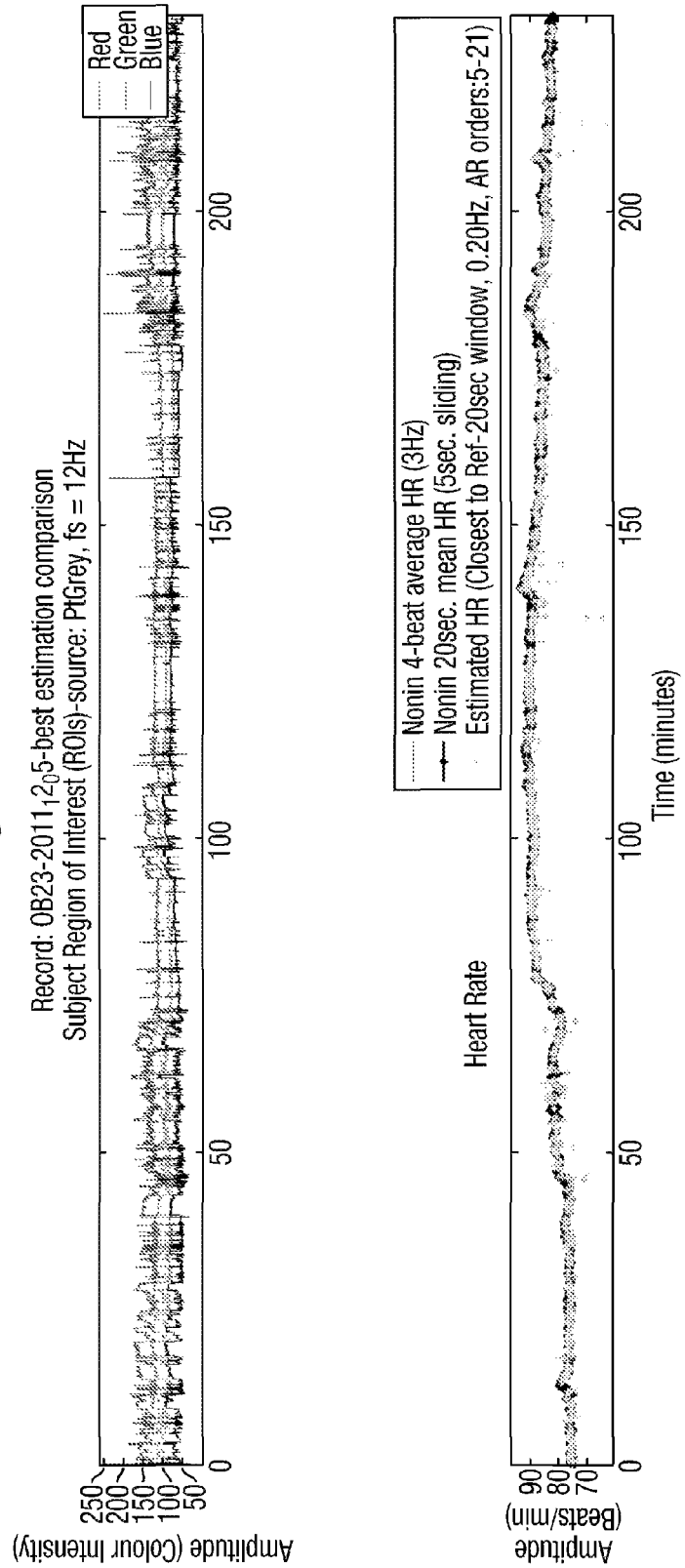
Figure 13A:
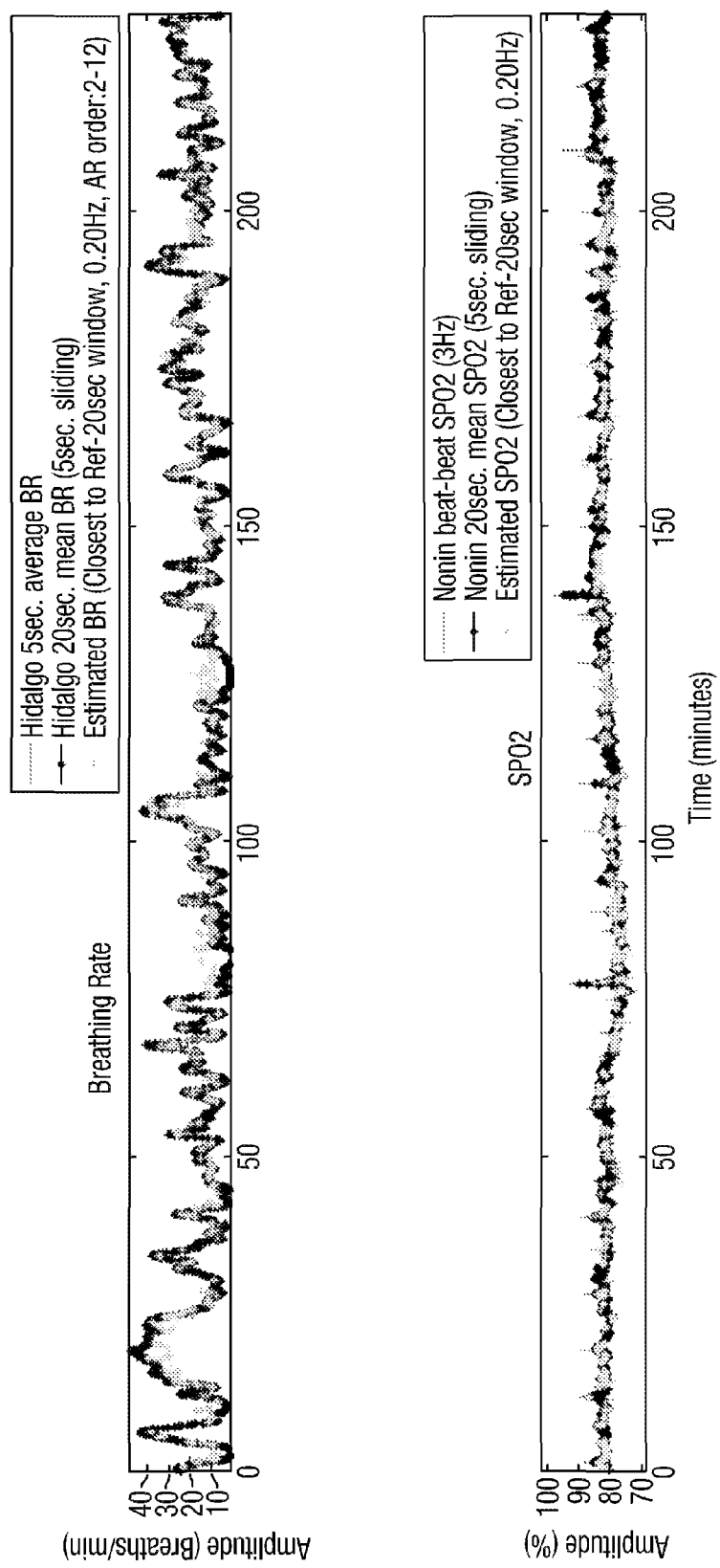
Figure 13B:
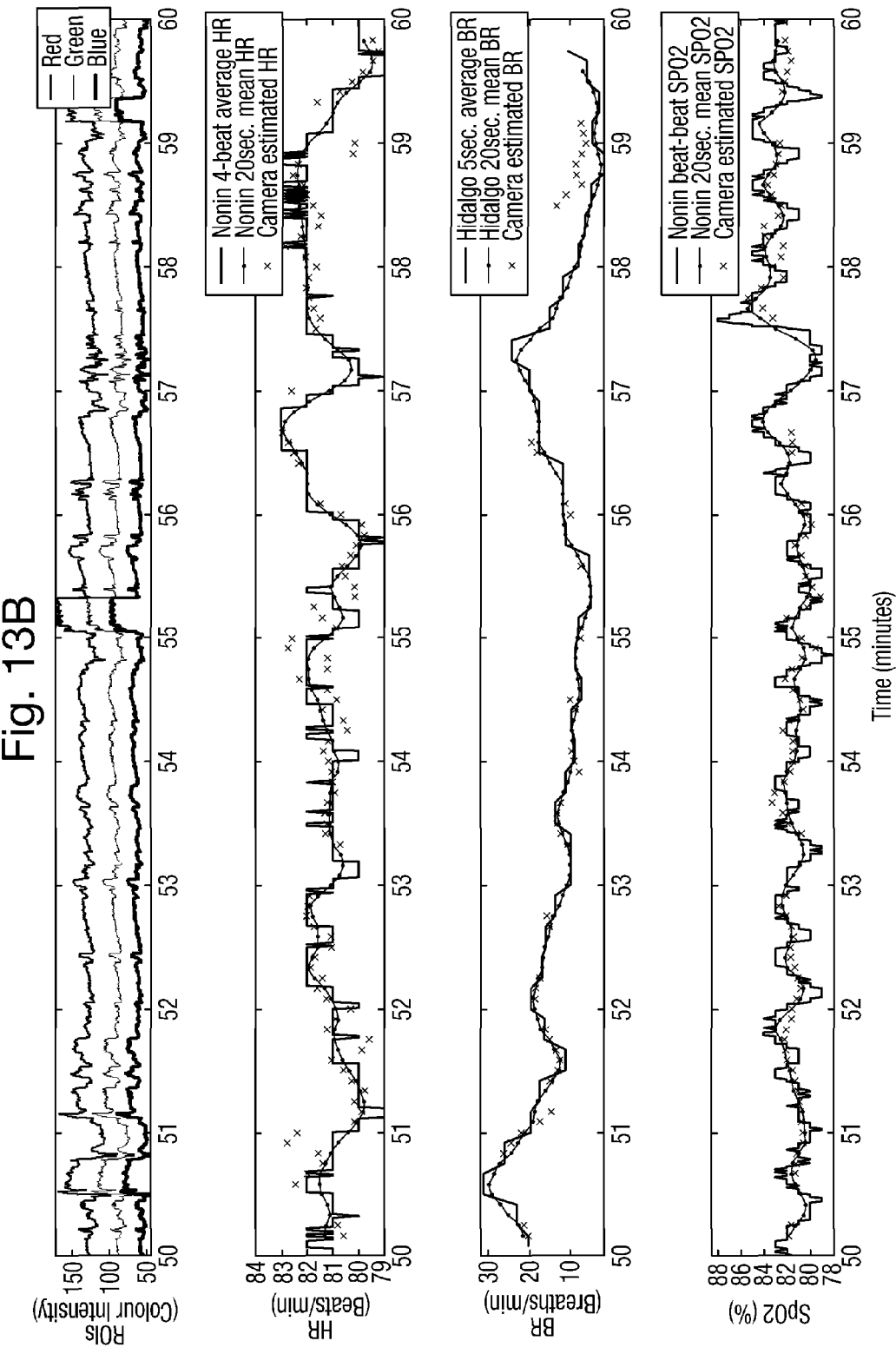
Figure 14A:
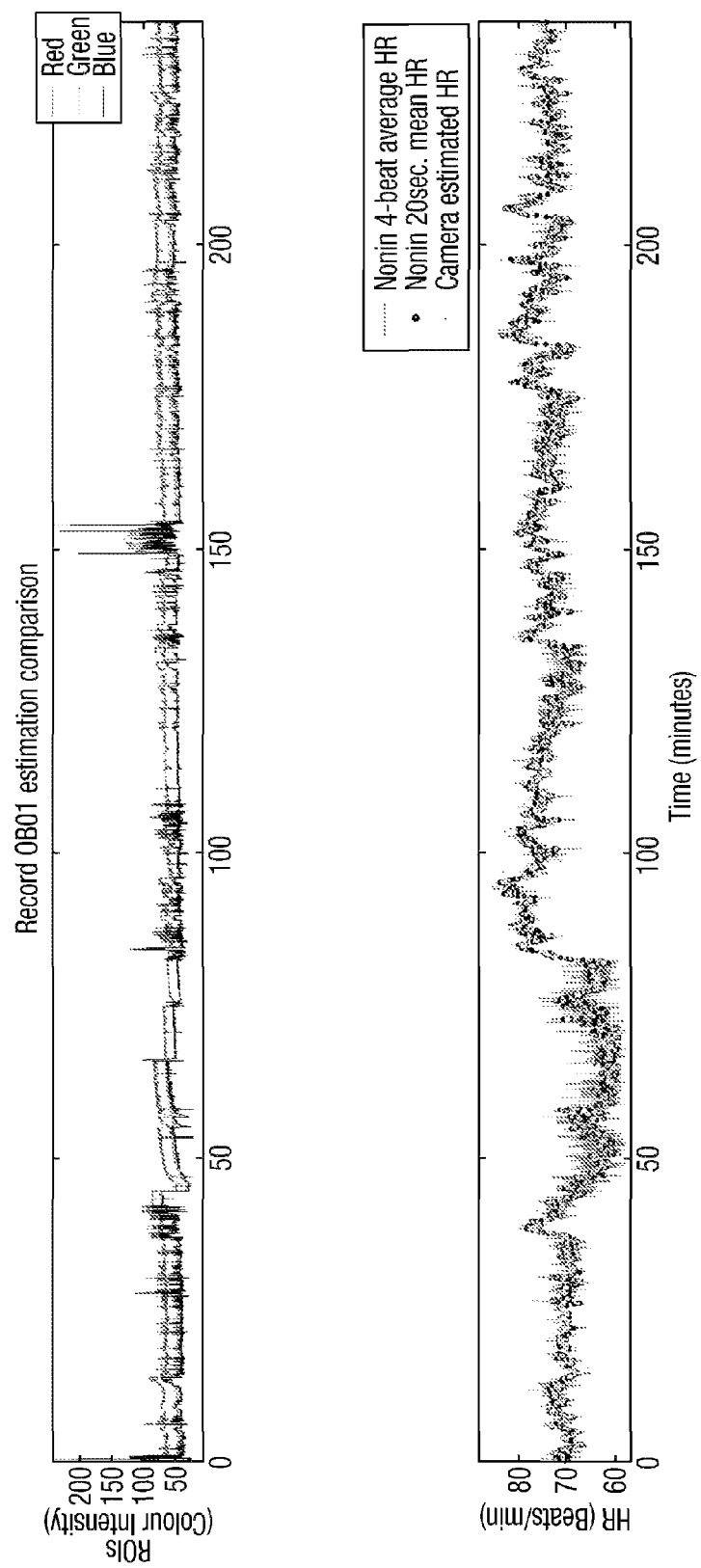
Figure 14A:
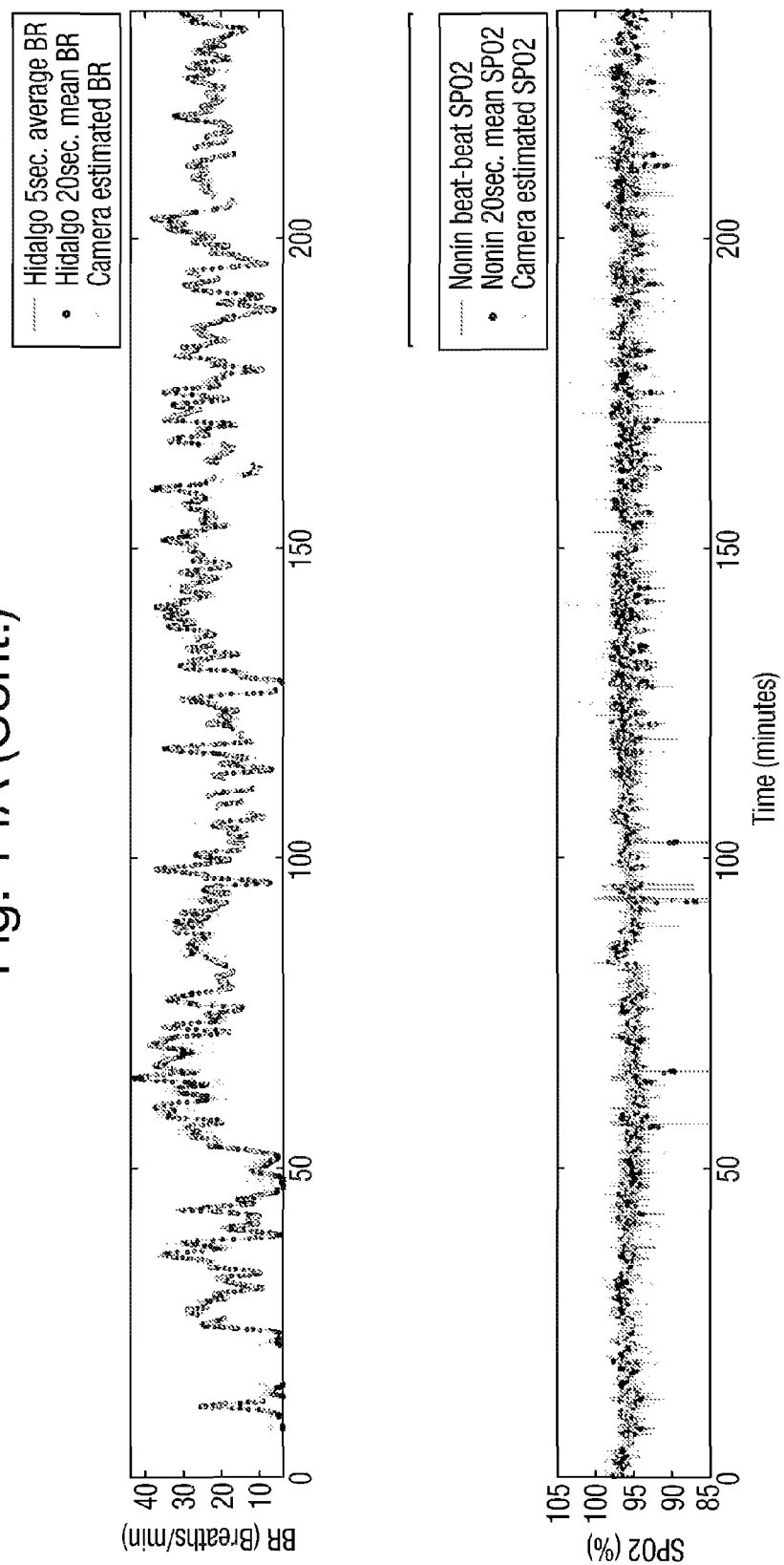
Figure 14B:
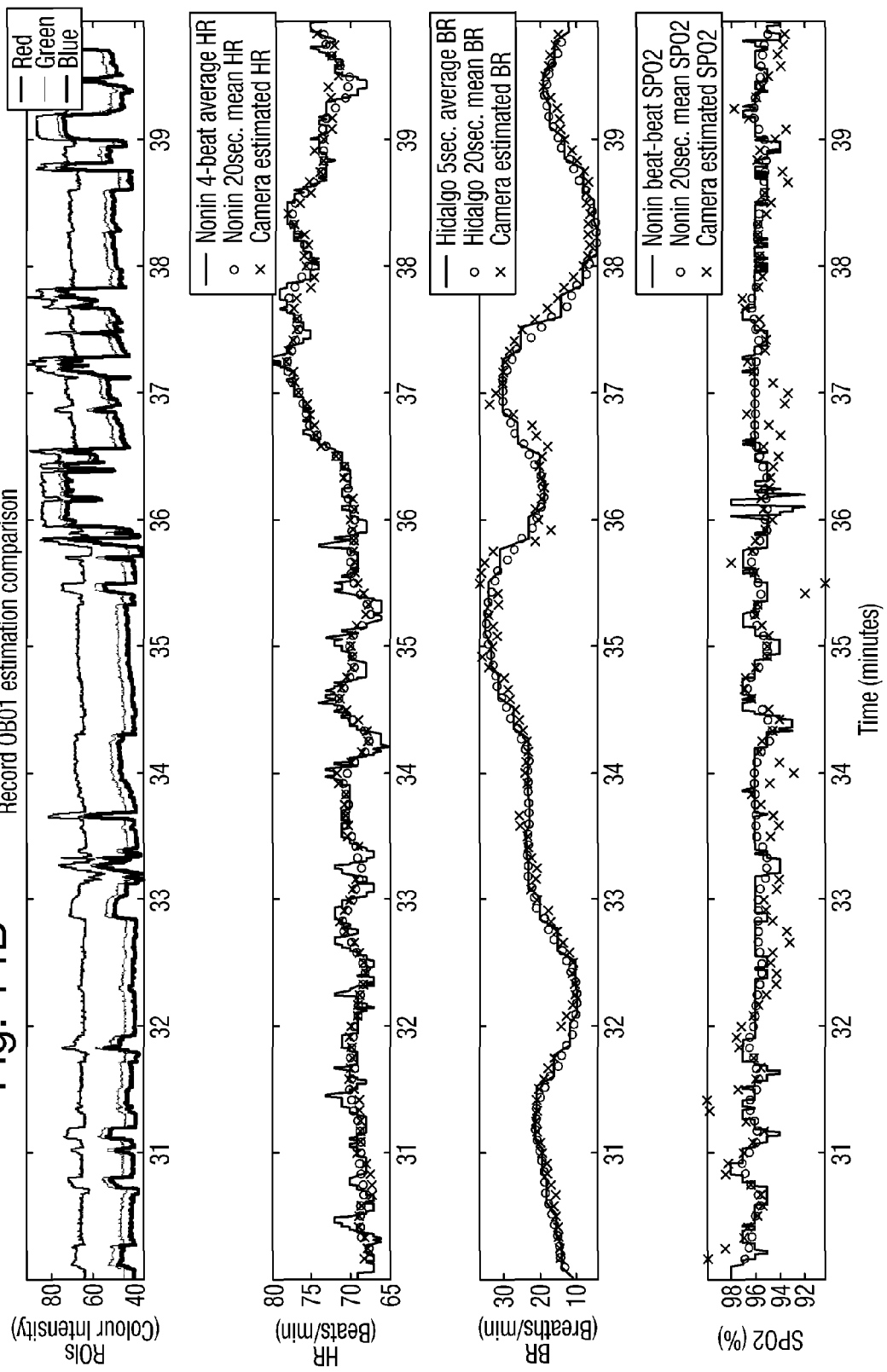
Figure 15A:
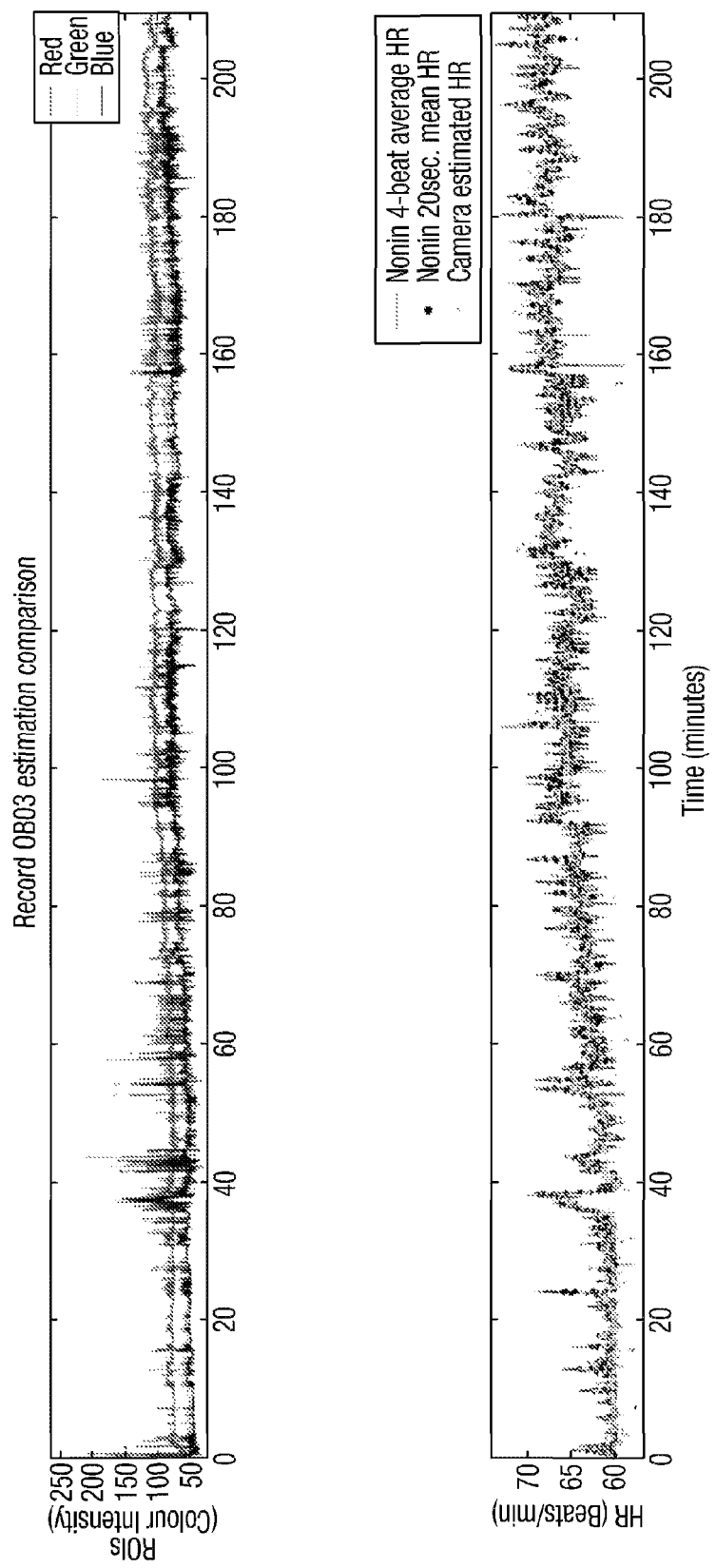
Figure 15A:
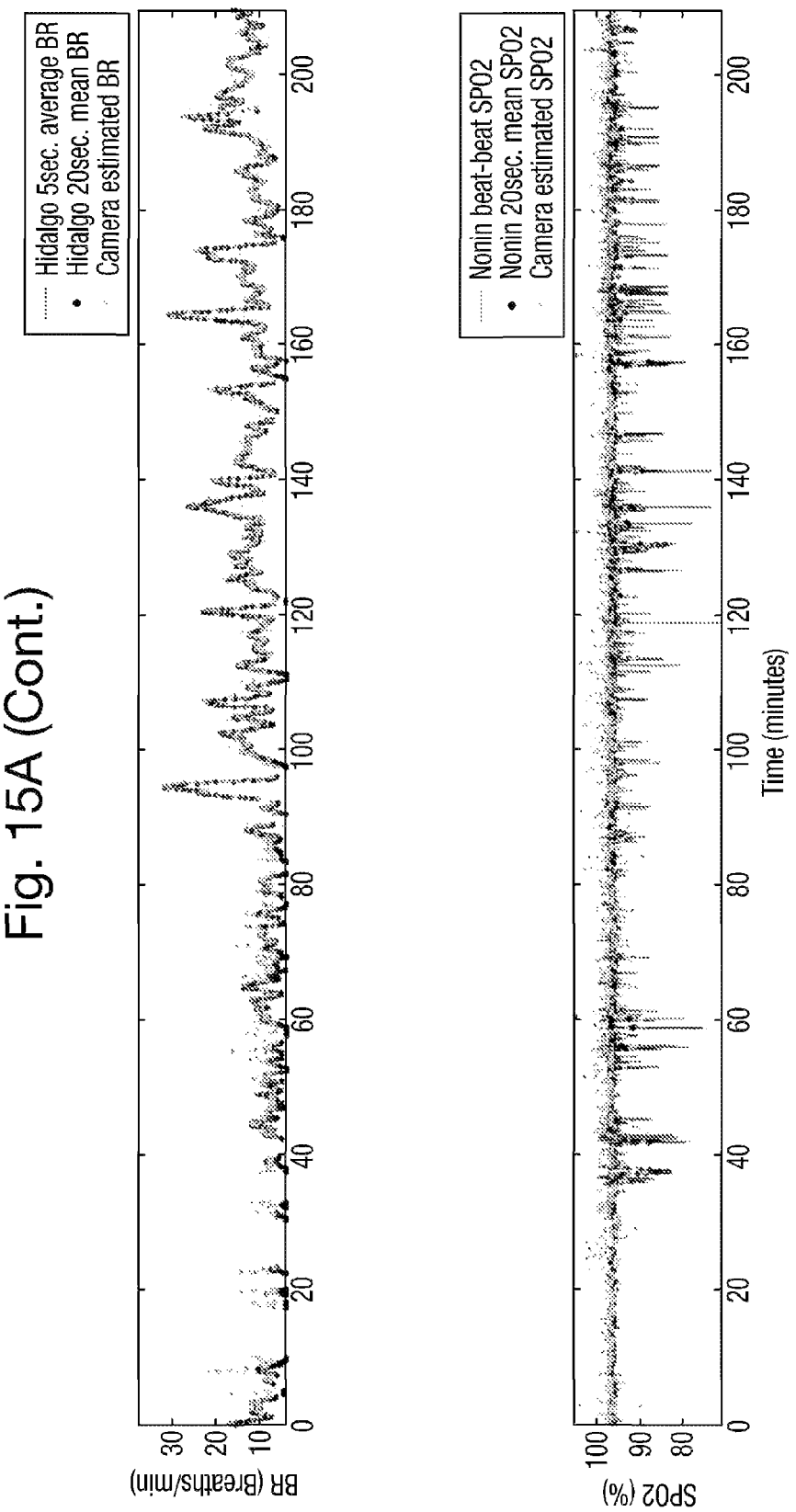
Figure 15B:
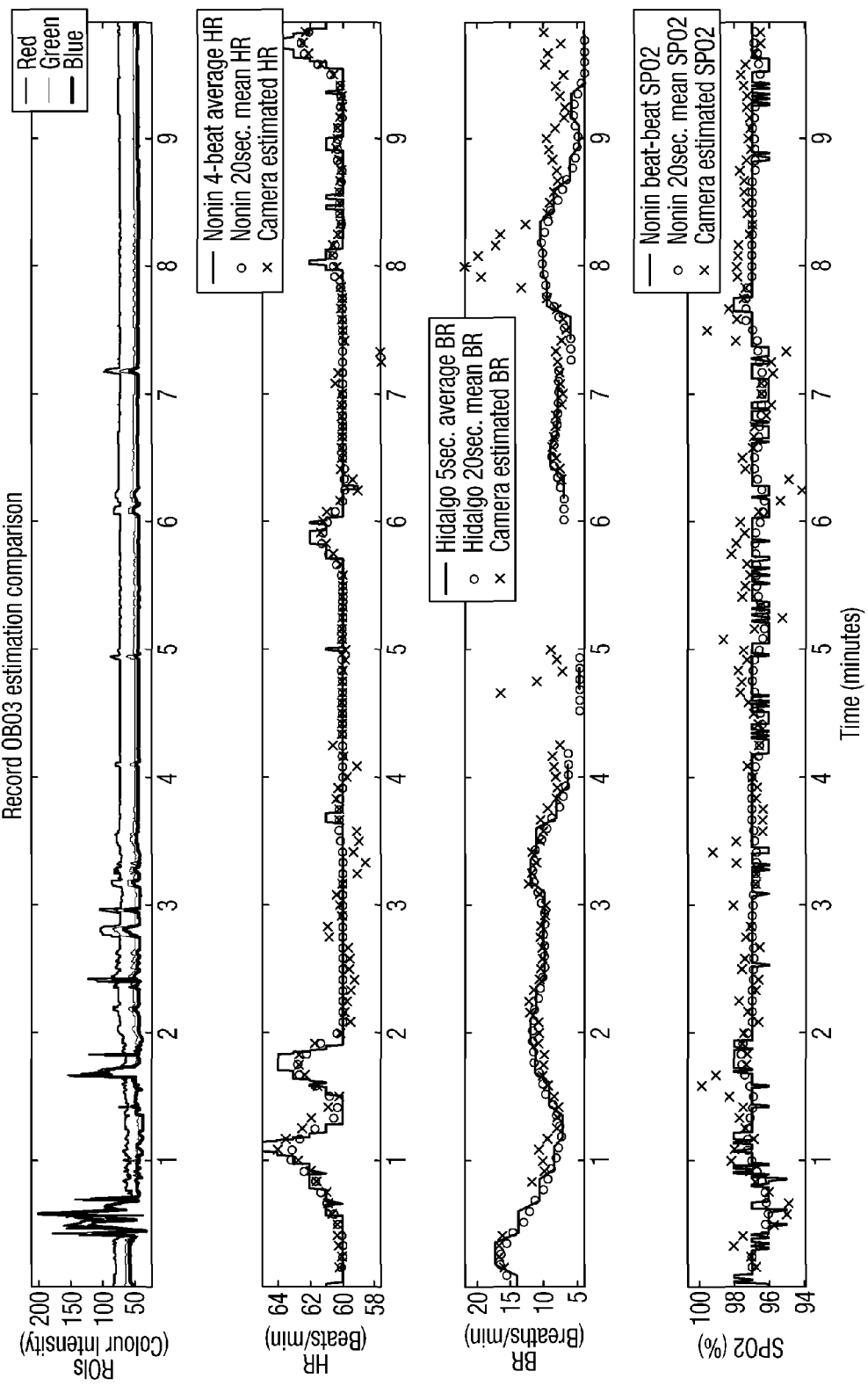
Figure 16A:
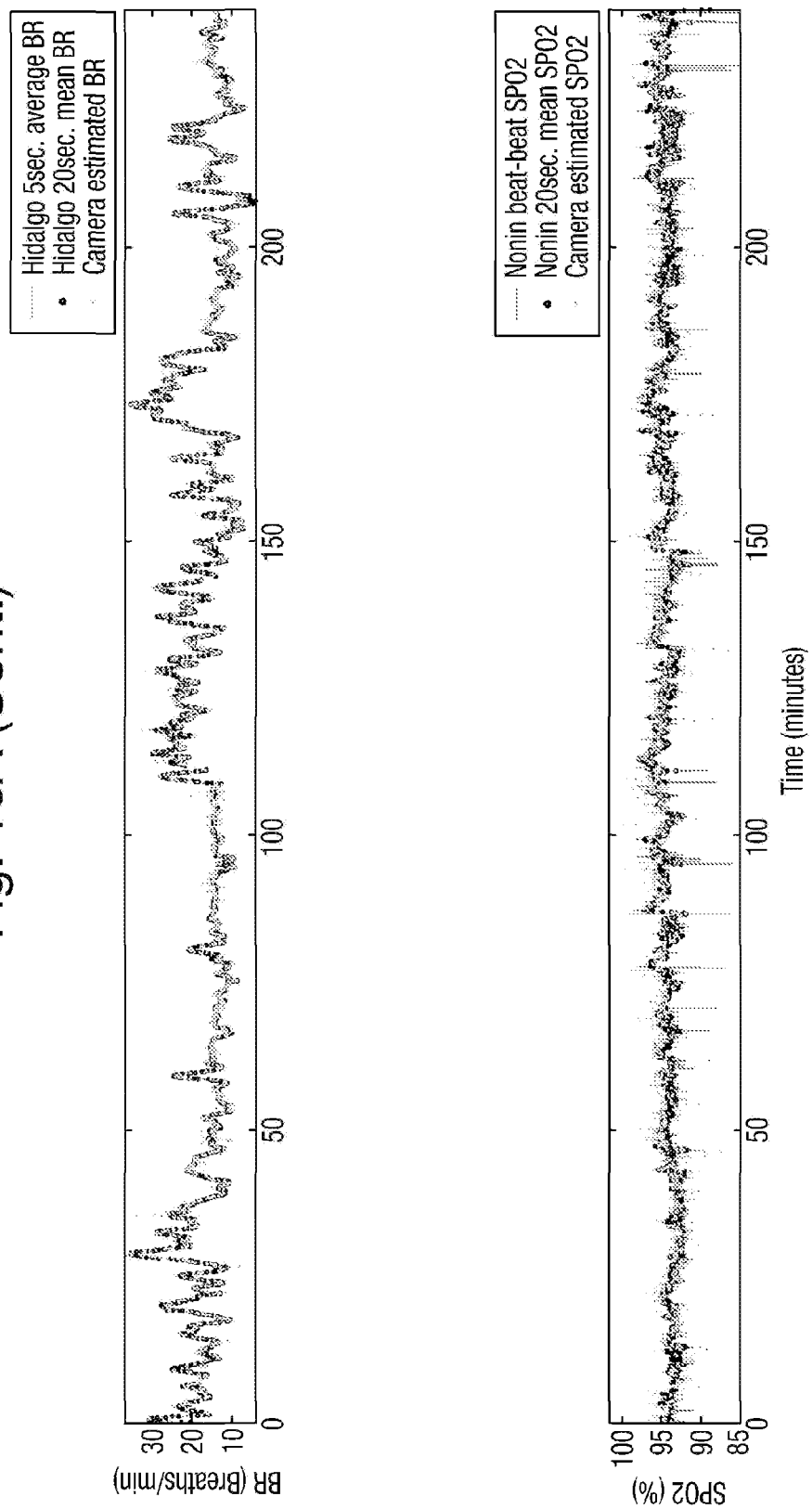
Figure 16B:
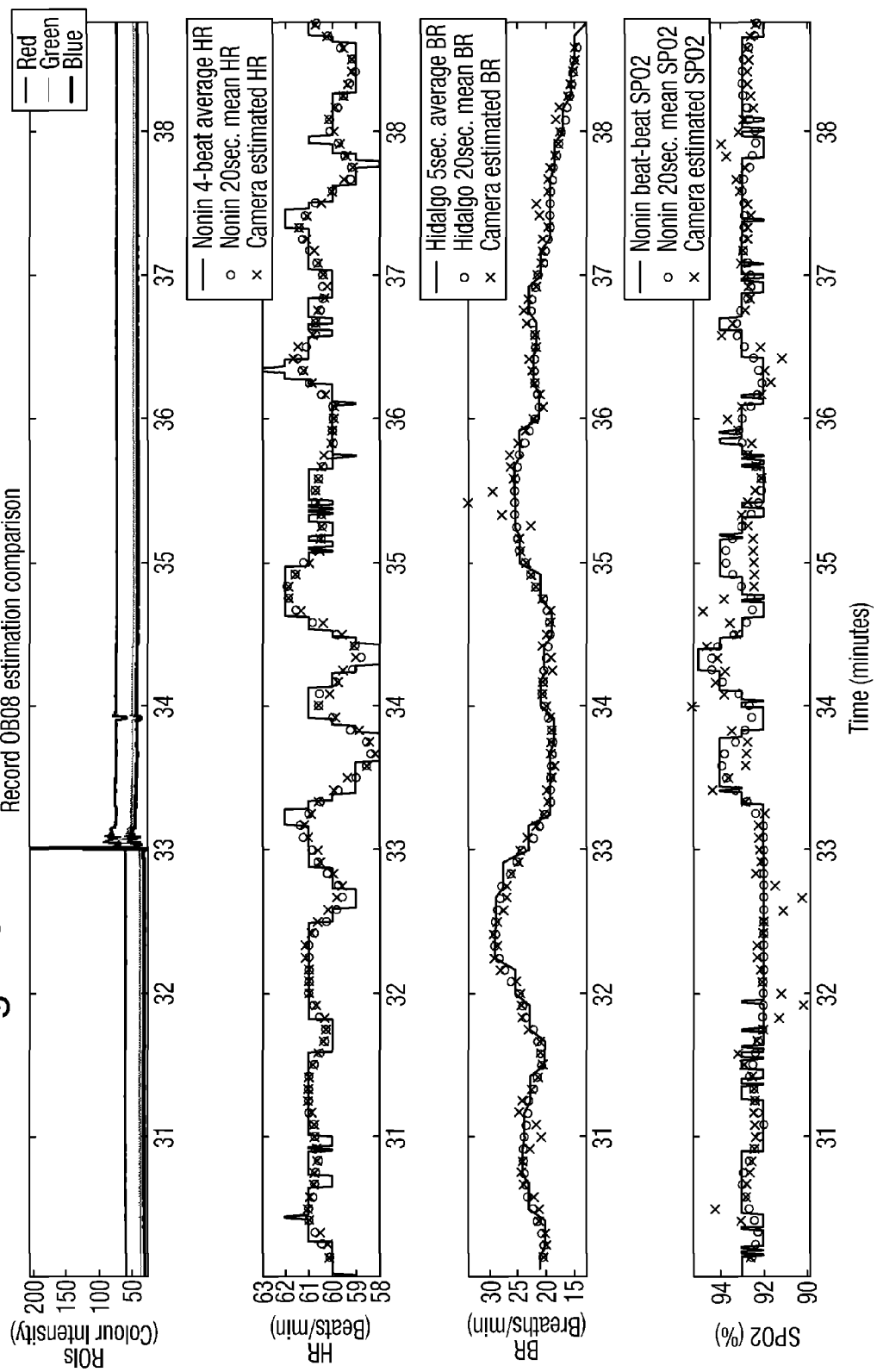

FIGS. 13A and B illustrate respectively, four hour and ten minute plots of the three colour intensities and heart rate, breathing rate and oxygen saturation estimates for an example patient together with conventionally measured values for the heart rate, breathing rate and oxygen saturation;

FIGS. 14A and B illustrate respectively, four hour and ten minute plots of the three colour intensities and heart rate, breathing rate and oxygen saturation estimates for another example patient together with conventionally measured values for the heart rate, breathing rate and oxygen saturation;

FIGS. 15A and B illustrate respectively, four hour and ten minute plots of the three colour intensities and heart rate, breathing rate and oxygen saturation estimates for another example patient together with conventionally measured values for the heart rate, breathing rate and oxygen saturation;

FIGS. 16A and B illustrate respectively, four hour and ten minute plots of the three colour intensities and heart rate, breathing rate and oxygen saturation estimates for another example patient together with conventionally measured values for the heart rate, breathing rate and oxygen saturation.

Figure 1A:
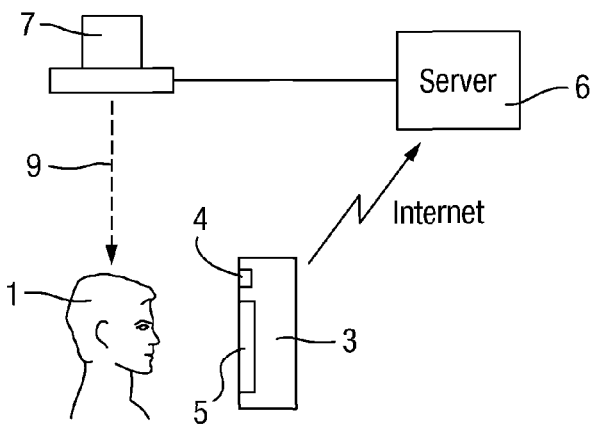

FIG. 1A schematically illustrates the vital-sign monitoring system in accordance with one embodiment of the invention. The vital-sign monitor itself is incorporated into a device 3 which has integrally provided within it a webcam 4 and screen 5. The device 3 can be a tablet or notebook computer, a mobile telephone (smartphone) or could be a television provided with a separate webcam 4. The patient 1 will be monitored by the webcam 4 while using the device 3 in their normal life, for example making a VOIP call or watching television. As will be explained below the device 3 is loaded with a software application which obtains the red, green and blue video output from the webcam 4 and analyses it to obtain vital-sign measurements. These measurements are stored and displayed to the patient (on demand) and are also sent via an internet connection to a remote server 6. The remote server 6 can be accessed by a clinician-based device 7 to allow a clinician to review the results and, if necessary, contact the patient either via a messaging application within the system itself or independently, for example, by telephone 9.

Figure 1B:
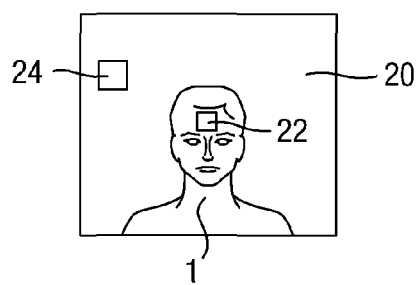
Figure 1C:
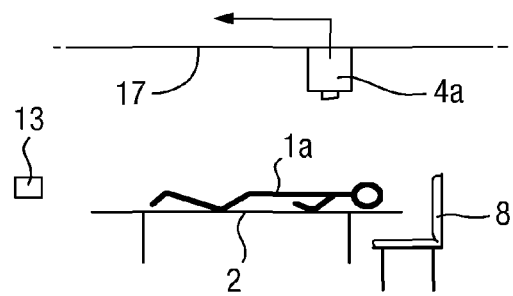

FIG. 1C illustrates a vital signs monitoring system in an embodiment of the invention intended for monitoring patients in hospitals. As illustrated, the vital signs monitor includes a video camera 4a mounted above the patient 1a, for example on the ceiling or a frame 17, where it can view the patient 1a while the patient is on a bed 2 or chair 8. The output from the video camera is supplied to a remote processing unit (not shown) for analysing the video signals as explained below. A wired or wireless controller 13 may be provided to control the video camera 4a. This embodiment of the invention is particularly useful for patients who are relatively immobile, for example acutely ill in-hospital patients or infants in neonatal incubators. Such patients typically have large exposed areas of skin over which the region or regions of interest for the analysis can be defined.

Figure 2:
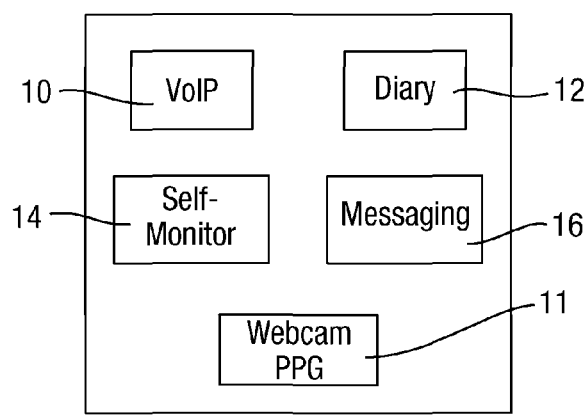
FIG. 2 illustrates the screen display to the patient in one embodiment of the invention.

FIG. 2 illustrates the screen display to the patient which is associated with the software application. In this embodiment the patient is presented with five icons to select five different functions. The first icon 10 is operable when selected to launch a VOIP application and also unobtrusively to start the webcam monitoring of the patient 1 to obtain the vital-sign measurements. The icon 11 is operable when selected to start the webcam monitoring of the patient 1 to obtain the vital-sign measurements. The icon 12 is operable when selected to display a patient diary into which the patient can enter information on their condition, and again this can also unobtrusively start the webcam monitoring of the patient 1 to obtain the vital-sign measurement. The icon 14 is operable when selected to guide the patient through a self monitoring process in which the patient can use conventional devices to obtain measurements of their vital signs, for example using a Bluetooth finger probe for heart rate, breathing rate and oxygen saturation measurement and a Bluetooth cuff for blood pressure measurement. Such measurements are sent to the device 3 using the Bluetooth connection and then via the internet to the server 6. Such measurements can be used to confirm the measurements obtained by analysis of the webcam video signal (e.g. if the clinician notices a deterioration in the subject's vital signs they can contact the subject to ask them to perform such a confirmation measurement). Finally the messaging icon 16 is operable when selected to start a messaging application allowing the patient to check messages received from a clinician.

FIG. 1B illustrates schematically the image obtained by the webcam 4. In general the image will contain an image of the patient 1 and background 20. In accordance with the invention one or more regions of interest ROIs 22 are defined on the subject, preferably on an area of skin, e.g. the face of the subject, and one or more reference regions of interest ROIr 24 are defined in the background. Conventional recognition algorithms can be used to find a suitable region in the image for the subject region of interest and for the background.

FIG. 3 sets out the process for analysing the signals from the webcam 4 to obtain a heart rate and oxygen saturation measurement. In steps 30 and 31 the ROIr 24 and ROIs 22 are defined. In step 32, for each video frame, for each of the three red, green and blue channels (or from the red channel of one video camera and from a second video camera with its IR filter removed to provide a signal in the infra-red region), one or more representative intensities from the region of interest, such as the spatial mean average or the modes of any distributions, are derived for both the ROIr and ROIs. In this embodiment the regions of interest are both 100 pixels by 100 pixels (i.e. 10,000 pixels total). However different size ROIs can be used and optionally multiple ROIs can be used. It is possible, in the limit, for each ROI to be centred on adjacent pixels.

Once the representative intensity for each frame has been obtained, a time series of these intensities is assembled for a series of frames in a time window of, for example, 30 seconds. The length of the time window can be varied, for example from 10 seconds to one minute.

In step 33 a plurality of auto-regressive (AR) models are fitted to each time series (that is to say to each of the red, green and blue time series from ROIr and to each of the red, green and blue time series from ROIs). Assuming a 24 frame per second video camera frame rate, for a 30-second window there will be 720 samples on each of the three channels for the reference background and for the subject. FIGS. 5A and 5B respectively show 30 second time series of data for the reference region of interest and for the subject region of interest.

It may be useful here to give a brief explanation of the general principles of autoregressive (AR) modelling, though AR modelling is well-known, for example in the field of speech analysis.

AR modelling can be formulated as a linear prediction problem where the current value $x(n)$ of the signal can be modelled as a linearly weighted sum of the preceding p values. Parameter p, which is the number of samples over which the sum is taken, is the model order, which is usually much smaller than the length N of the sequence of values forming the signal. Thus:—

$$x(n) = -\sum_{k=1}^{p} a_k x(n-k) + e(n) \tag{1}$$

The value of the output x(n) is therefore a linear regression on itself, with an error e(n), which is assumed to be normally distributed with zero mean and a variance of $\sigma^2$. More usefully for this application the model can alternatively be visualised in terms of a system with input e(n), and output x(n), in which case the transfer function H can be formulated as shown below:

$$H(z) = \frac{1}{\sum_{k=1}^{p} a_k z^{-k}} = \frac{z^p}{(z-z_1)(z-z_2) \ldots (z-z_p)} \quad (2)$$

As shown in Equation 2, the denominator of H(z) can be factorised into p terms. Each of these terms defines a root $z_i$ of the denominator of H(z), corresponding to a pole of H(z). Since H(z) has no finite zeros, the AR model is an all-pole model. The poles occur in complex-conjugate pairs and define spectral peaks in the power spectrum of the signal. They can be visualised in the complex plane as having a magnitude (distance from the origin) and phase angle (angle with the positive real axis). Higher magnitude poles correspond to higher magnitude spectral peaks and the frequency of each spectral peak is given by the phase angle of the corresponding pole. The phase angle θ corresponding to a given frequency f, is defined by Equation 3 which shows that it is also dependent on the sampling interval Δt (reciprocal of the sampling frequency):

$$\theta = 2\pi f \Delta t \quad (3)$$

Thus fitting a suitable order AR model to a signal, and obtaining the poles, reveals the spectral composition of the signal.

To find the poles, the model parameters $a_k$ are first obtained, for example using the Burg or Yule-Walker equations to fit the model to the signal, and from the values of $a_k$ the values of the p poles $z_1$ to $z_p$ can be calculated (see, for example, Pardey J, Roberts S, Tarassenko L, A review of parametric modelling techniques for EEG analysis, *Medical Engineering & Physics*, 1996, 18(1), 2-11). The p poles of H(z), which correspond to the p roots $z_i$ (i=1 to p) of the denominator of H(z) are found using standard mathematical procedures (for example, the MATLAB routine roots). As each pole $z_k$ can be written as a complex number $x_k + jy_k$, the frequency represented by that pole can be calculated from the phase angle of that pole in the upper half of the complex plane:

$$\theta = \tan^{-1} y/x = 2\pi f_k \cdot 1/f_s \quad (4)$$

where $f_s$ is the sampling frequency and the magnitude r is $(x^2+y^2)^{1/2}$.

Thus the AR model fitting of step 33 reveals the dominant spectral components in both the signal from the reference region of interest and the PPG image signal from the subject region of interest. Because the two regions of interest are both imaged by the same camera, any ambient light interference or aliasing artefacts will be present in both the reference and the PPG signal. However the signal from the subject region of interest will additionally have poles corresponding to spectral components representing the PPG signal. FIGS. 6A and 6B illustrate respectively the spectral content of the reference and subject regions of interest obtained by fitting the twelfth order AR model to the 30-second window of data of FIGS. 5A and 5B. FIGS. 6D and 6E show the position of the poles derived from this twelfth order model. As mentioned above, corresponding poles are identified in the different order models (8 through 20) fitted to the same data.

In step 34 any poles in the AR model fitted to the subject data of FIG. 6D which are also present in the AR model fitted to the reference signal are cancelled. Poles are regarded as present in both the subject and reference regions of interest if they are within a few angular degrees of each other, typically one or two degrees. In step 35 any pole remaining which also lies outside the allowed range for heart rate are removed. These are poles with angles greater than 60° (if the sampling frequency is 24 Hz, 180° corresponds to 12 Hz and so 60° corresponds to 4 Hz which is 240 beats per minute). Also any poles at angles less than 10° (i.e. corresponding to 0.67 Hz or below or less than 40 beats per minute) are removed.

Then in step 36 the remaining pole which is closest to the horizontal axis, i.e. has the minimum angle and thus the lowest frequency in the allowed range is identified and the frequency it represents calculated. Alternatively, as represented by step 36a it is possible to obtain the frequency response of the filter characterised by the $a_k$ coefficients of Eq. (1) and to select the frequency which has the largest magnitude in the frequency response. This is the frequency which corresponds to the subject's heart rate. In the data of FIGS. 5 and 6 the remaining heart rate pole is illustrated in FIG. 6F. FIG. 6C illustrates the corresponding plot of spectral content after cancellation of the poles.

These steps are conducted on all of the different order AR models fitted to the same 30-second window of data and in step 37 a robust estimate of the resulting heart rate estimates is obtained, for example the median value. This value is stored and displayed in step 38 and then in step 39 the 30-second window is moved forward by 1 second and steps 33 to 38 repeated. The heart rate estimates are sent in step 40 to the remote server 6.

In FIG. 6F the pole identified as the heart rate is at an angle of 17.7° which corresponds to a frequency of 1.18 Hz and hence a heart rate of 71 bpm.

The AR fitting method above also allows for the oxygen saturation to be measured. In FIG. 6F the radius of the pole, i.e. its distance from the origin, is an indication of the amplitude of the heart rate component in that (red, green or blue) channel. Thus in step 42 the radius of the heart rate pole in the green (or infra-red) channel and the red channel is obtained and the ratio of the radii is taken. This corresponds to the ratio of the reflected intensities at the red and green (or infra-red) wavelengths. The $SpO_2$ value can be calculated from this ratio using calibration tables. The calibration tables are obtained from studies in which human volunteers or patients are double-monitored. With human volunteers, this means de-saturating the subjects (usually down to $SpO_2$ values of 80%) under supervised, controlled conditions in studies for which Medical Research Ethics Committee approval has been obtained. Blood samples are withdrawn at regular samples to measure the oxygen saturation using a blood gas analyser (see, for example, Moyle JTB, Pulse Oximetry (Principles and Practice), BMJ Publications, 2002). The alternative is to monitor patients who regularly de-saturate naturally, for example renal patients during a dialysis session, both with one or more webcams and with a calibrated, commercially-available pulse oximeter, from which the reference values of $SpO_2$ are obtained during the dialysis session. The $SpO_2$ value is stored and displayed at step 44 and can be sent to the remote server 6 in step 40.

FIG. 7B illustrates a comparison of the 30-second mean heart rate estimates (the darker, thicker line) obtained by the embodiment of the invention above (from the colour intensity amplitudes illustrated in FIG. 7A) with 4 beat and 8 beat average heart rate measurements from a standard pulse oximeter device and finger probe (the lighter, thinner lines). It can be seen that the agreement between the two different methods is good.

FIG. 4 illustrates a method of obtaining the breathing rate from the PPG image signal from the webcam 4. The method corresponds to the method used for obtaining the heart rate and illustrated in FIG. 3, except that an additional step 40 is included in which the time series of average intensities is low-pass filtered and downsampled in this embodiment to a frequency of, for example, 4 Hz (by taking every sixth sample, assuming a 24 frame per second camera frame rate). The low-pass filter prior to the downsampling process has its cut-off frequency set such that all frequencies above $f_d/2$ (where $f_d$=downsampling frequency, i.e. 4 Hz in this example) are eliminated prior to the downsampling process. As with FIG. 3, in step 33' several models, in this case of order 4 to 20, are then fitted to each 30-second window of data, corresponding poles are cancelled in step 34' and poles which are outside the allowed range for breathing rate cancelled in step 35'. In step 36' the breathing rate pole is identified by looking for poles in an allowable range for breathing rate, e.g. 0.06 Hz to 0.7 Hz (3.6 to 42 breaths per minute). Then the pole closest to the horizontal axis, i.e. the lowest frequency in the allowable range, is taken and the breathing rate it represents is calculated from its angle. Alternatively, as represented by step 36a' it is possible to obtain the frequency response of the filter characterised by the $a_k$ coefficients of Eq. (1) and to select the frequency which has the largest magnitude in the frequency response. The values from the different order models are fused (e.g. by taking the median) to produce a robust estimate, as with the estimation of heart rate, and the results stored, displayed and sent to the server in steps 37' to 40'.

FIGS. 8A and 8B illustrate respectively the downsampled time series of intensity values from the reference region of interest and subject region of interest of FIG. 5, together with their main frequency components calculated using the Fast Fourier Transform (FFT). FIGS. 9A, 9B and 9C illustrate the pole plots for the reference region of interest (FIG. 9A), the subject region of interest (FIG. 9B), and for the subject region of interest (FIG. 9C) after cancellation of the poles corresponding to those found in the reference region of interest. In the illustrated plots the remaining pole above the horizontal axis is at an angle of 17°, corresponding to a frequency of 0.19 Hz and a breathing rate of 11 breaths per minute.

FIGS. 13A and B, 14A and B, 15A and B and 16A and B show for four different patients measurements of the red, green and blue colour intensities together with the heart rate, breathing rate and oxygen saturation ($SpO_2$) estimated using an embodiment of the invention plotted with measurements of the heart rate, breathing rate and oxygen saturation obtained by conventional means. FIGS. 13A, 14A, 15A and 16A all show four hour periods (actually for patients undergoing dialysis), while FIGS. 13B, 14B, 15B and 16B show a ten minute section of the four hour period in more detail. It can be seen that the agreement for each of the heart rate, breathing rate and oxygen saturation between the estimate obtained with the embodiment of the invention and the conventional measurement is good. Furthermore, the agreement between the estimate according to this embodiment of the invention and the conventional measurement is good for the four patients who have different heart rates, breathing rates and oxygen saturations.

Previous work on acutely ill patients has shown how the distributions of vital signs in a population of such patients can be used to compute an Early Warning Score, the value of which increases with the severity of illness. FIG. 10 shows histograms for the four main vital signs: heart rate, breathing rate, arterial oxygen saturation and systolic blood pressure, obtained from patients in acute care in three hospitals in the UK and the US. The central vertical line indicates the mean of the data, with the two vertical lines either side corresponding to one standard deviation (except for $SpO_2$, which has a one-sided distribution). Histograms are estimates of the probability density function p(x) for the random variable x. The cumulative distribution function (cdf), P(x), is the integral of p(x). The cdfs for each vital sign are shown in FIG. 11.

The Early Warning Score was obtained by constructing an alerting system using the hypothesis that an Early Warning Score (EWS) of 3 should be generated when a vital sign is below the 1st centile or above the 99th centile for that variable (for a double-sided distribution), a score of 2 should correspond to the vital sign being between the 1st and 5th centiles or between the 95th and 99th centiles and that a score of 1 should correspond to the vital sign being between the 5th and 10th centiles or between the 90th and 95th centiles. (For $SpO_2$, with a one-sided distribution starting at 100%, values above the 98th centile will give a score of 3, values between the 90th and 98th centiles a score of 2, and values between the 80th and 90th centiles a score of 1). The vertical lines on the cdf plots of FIG. 11 allow the cut-off values to be determined for each vital sign. To take breathing rate as an example, 1% of patients had a breathing rate ≤7 breaths/min, 5% a rate ≤10 breaths/min, and 10% a rate ≤13 breaths/min. At the upper end, 90% of patients had a breathing rate ≤26 breaths/min, 95% a rate ≤29 breaths/min and 99% a rate ≤34 breaths/min.

In the EWS systems currently used in hospitals, the scores for each individual vital sign are quantised with integer precision (i.e. they can only take on a value of 0, 1, 2 or 3). There is no reason why this should be the case as the cdf curves are smooth, however, and in this embodiment of the invention a wellness index with a much smaller quantisation (steps of 0.1 for each vital sign) is used. A set of curves for an EWS system with 0.1 quantisation in the range from 1 to 3 is shown in FIG. 12.

A sick in-hospital patient will have a high EWS score (a score of 3 for three vital signs, for example, will give an EWS of 9). In this embodiment a wellness score is calculated instead which decreases with vital sign abnormality. For example, a patient with normal heart rate, normal breathing rate and normal $SpO_2$, will have a cardio-respiratory wellness index of 10. The further away from the centre of the distributions any vital sign is, the lower the value of the cardio-respiratory wellness index will be. For example, if the wellness index is derived from the heart rate (HR), respiratory rate/breathing rate [RR/BR] and $SpO_2$, estimated as described above, the wellness index could be obtained from the simple formula:

$$\text{Index}=10.0-\{\text{score}[HR]+\text{score}[RR/BR]+\text{score}[SpO_2]\}$$

where the score is for each parameter is read off from the y-axis on the plot for that parameter on FIG. 12.

In the case of having a measurement of blood pressure also, then the four distributions will be used to derive a cardiovascular index of wellness, also on a scale from 0 to 10.

Over time, it is possible to design a patient-specific set of wellness indices. This requires sufficient vital sign data to be collected, over the full range of daytime hours, so that histograms and cdfs for that individual can be constructed. Once this has been achieved, a centile-based wellness index which is patient-specific can be created.

Another important aspect of this invention is that the vital signs can be uniquely linked to the individual whose physiology they represent, through face recognition software. With the usual methods for the remote monitoring of vital signs, there is no guarantee that the vital signs are those of the individual presumed to have generated them, as the probes or electrodes could be attached to anyone in the vicinity of the individual (with or without their knowledge). With this invention, any uncertainty as to the origin of the vital signs is removed as the face of the subject is captured by the camera during the estimation of the values of the vital signs.

While the embodiments of the invention above have concentrated on use by subjects at home, they are equally applicable to use in a hospital setting. For good signals to be obtained the subject needs to be relatively still in front of the camera, but in a hospital this can be the case in a critical care or neo-natal unit and thus the invention is useful in these cases too. The invention is applicable in any PPG imaging situation. For example PPG imaging could be used for screening for those suffering from infections which often elevates heart rate and breathing rate, such screening being useful at for example points of entry such as ports, airports and building entrances. It can also be useful as part of the parameter detection used in lie detection.

The invention claimed is:

1. A method of suppressing ambient light interference in a photoplethysmographic (PPG) image signal, the method comprising:
    imaging a first region of interest on a skin of a subject using a video camera to obtain a PPG image signal, wherein the PPG image signal comprises periodic intensity variations corresponding to ambient light reflected from the region of interest;
    imaging a first reference region of interest not on the skin using the video camera to obtain a reference signal;
    spectrally analyzing, via a computer, the reference signal using a first auto-regressive (AR) all pole model to identify poles corresponding to spectral components in the first AR all pole model for the reference signal; and
    spectrally analyzing, via a computer, the PPG image signal using a second auto-regressive (AR) all pole model to identify poles corresponding to spectral components in the second AR all pole model for the PPG image signal and removing poles in the second AR all pole model corresponding to the spectral components of the reference signal to suppress the ambient light interference;
    estimating, via the computer, a first vital-sign of the subject based on a remaining portion of the second AT all pole model and after removal of the selected ones of the poles from the second AR all pole model corresponding to the spectral components of the reference signal; and
    storing, displaying or transmitting, via the computer, the estimated first vital sign.

2. The method according to claim 1, wherein the reference signal and PPG image signal are output signals from (i) at least one of red, green and blue channels of the video camera, or (ii) an infrared channel of another camera.

3. The method according to claim 1, further comprising:
    imaging a first plurality of regions of interest on the skin, wherein the first plurality of regions of interest include the first region of interest; and
    imaging a second plurality of regions of interest, wherein the second plurality of regions of interest comprise the reference region of interest and other reference regions of interest.

4. The method according to claim 3, wherein each of the first plurality of regions of interest and each of the second plurality of regions of interest is centered on a single camera pixel.

5. The method according to claim 1, further comprising obtaining vital sign data from remaining components of the PPG image signal.

6. The method according to claim 1, wherein:
    the reference signal and the PPG image signal are each analyzed using a plurality of models having respective orders; and
    the plurality of models comprise the first AR all pole model and the second AR all pole model.

7. The method according to claim 6, wherein the plurality of models have respectively orders 8 to 20.

8. The method according to claim 6, further comprising averaging the spectral components of the reference signal and the PPG image signal over different order models, wherein the different order models include the first AR all pole model and the second AR all pole model.

9. The method according to claim 1, further comprising obtaining a measurement of a heart rate of the subject by identifying a pole in the PPG image signal as representing the heart rate, which is not present in the reference signal.

10. The method according to claim 9, wherein the measurement of the heart rate is obtained by identifying a pole corresponding to a spectral component and having a frequency between 0.67 Hz and 4 Hz.

11. A method according to claim 9, further comprising obtaining a measurement of a blood oxygen saturation level of the subject by obtaining a ratio of intensity of light at two different wavelengths reflected from the region of interest on the skin, wherein the intensity of light is obtained from a magnitude of the pole identified as representing the heart rate.

12. A method according to claim 11, wherein the two different wavelengths are red and green wavelengths detected by the video camera.

13. A method according to claim 11, wherein the two different wavelengths comprise (i) a red wavelength detected by the video camera, and (ii) an infrared wavelength detected by a second video camera.

14. A non-transitory computer readable storage medium storing software executable by at least one of a processor and a controller, wherein the software includes code adapted to:
    execute the method of claim 1; and
    obtain a measurement of one or more vital signs of the subject by PPG imaging the subject, wherein the one or more vital signs include the estimated first vital sign, and wherein ambient light interference associated with the PPG imaging is suppressed by execution of the method of claim 1.

15. A method of measuring one or more vital signs including the first vital sign, the method comprising:

PPG imaging the subject using the video camera including suppressing the ambient light interference by performing the method of claim 1; and performing a facial recognition process on an image of the subject obtained by the video camera to link the identity of the subject to the one or more vital signs.

16. A method according to claim 1, further comprising obtaining a measurement of a breathing rate of the subject by low-pass filtering and downsampling the PPG image signal before spectrally analyzing the PPG image signal using a third AR all pole model.

* * * * *